United States Patent
Sakamoto et al.

(10) Patent No.: US 10,227,292 B2
(45) Date of Patent: Mar. 12, 2019

(54) POLYMERIZABLE COMPOUND, POLYMERIZABLE COMPOSITION, POLYMER, AND OPTICALLY ANISOTROPIC BODY

(71) Applicant: ZEON CORPORATION, Tokyo (JP)

(72) Inventors: Kei Sakamoto, Tokyo (JP); Satoshi Kiriki, Tokyo (JP); Kumi Okuyama, Tokyo (JP); Kanako Sanuki, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 733 days.

(21) Appl. No.: 14/768,016

(22) PCT Filed: Feb. 12, 2014

(86) PCT No.: PCT/JP2014/053215
§ 371 (c)(1),
(2) Date: Aug. 14, 2015

(87) PCT Pub. No.: WO2014/126113
PCT Pub. Date: Aug. 21, 2014

(65) Prior Publication Data
US 2016/0002374 A1  Jan. 7, 2016

(30) Foreign Application Priority Data

Feb. 15, 2013 (JP) ................. 2013-027240

(51) Int. Cl.
| | |
|---|---|
| *C09K 19/38* | (2006.01) |
| *G02B 5/30* | (2006.01) |
| *C08F 22/10* | (2006.01) |
| *C09K 19/04* | (2006.01) |
| *C09K 19/30* | (2006.01) |
| *C09K 19/32* | (2006.01) |
| *C09K 19/34* | (2006.01) |
| *C07C 251/88* | (2006.01) |
| *C07D 277/82* | (2006.01) |
| *C08F 128/06* | (2006.01) |
| *C08F 222/10* | (2006.01) |

(52) U.S. Cl.
CPC .......... *C07C 251/88* (2013.01); *C07D 277/82* (2013.01); *C08F 22/10* (2013.01); *C08F 128/06* (2013.01); *C09K 19/3068* (2013.01); *C09K 19/32* (2013.01); *C09K 19/3497* (2013.01); *C09K 19/3809* (2013.01); *G02B 5/3025* (2013.01); *C08F 2222/102* (2013.01); *C09K 2019/0444* (2013.01); *C09K 2019/0448* (2013.01); *C09K 2019/3075* (2013.01)

(58) Field of Classification Search
None
See application file for complete search history.

(56) References Cited

U.S. PATENT DOCUMENTS

| | | | |
|---|---|---|---|
| 5,567,349 A | 10/1996 | Kelly et al. | |
| 6,139,771 A | 10/2000 | Walba et al. | |
| 6,203,724 B1 | 3/2001 | Reiffenrath et al. | |
| 6,565,974 B1 | 5/2003 | Uchiyama et al. | |
| 2002/0159005 A1 | 10/2002 | Arakawa et al. | |
| 2003/0102458 A1 | 6/2003 | Nishikawa et al. | |
| 2007/0176145 A1 | 8/2007 | Nishikawa et al. | |
| 2007/0298191 A1 | 12/2007 | Yamahara et al. | |
| 2009/0072194 A1 | 3/2009 | Yamahara et al. | |
| 2009/0189120 A1 | 7/2009 | Takeuchi | |
| 2010/0201920 A1 | 8/2010 | Adlem et al. | |
| 2010/0301271 A1 | 12/2010 | Adlem et al. | |
| 2014/0107247 A1* | 4/2014 | Sakamoto | C09K 19/32 522/39 |
| 2015/0175564 A1 | 6/2015 | Sakamoto et al. | |

FOREIGN PATENT DOCUMENTS

| | | |
|---|---|---|
| JP | 10-068816 A | 3/1998 |
| JP | 10-090521 A | 4/1998 |
| JP | 2000-284126 A | 2/1999 |
| JP | 2000-284126 A | 10/2000 |
| JP | 2001-004837 A | 1/2001 |
| JP | 2002-267838 A | 9/2002 |
| JP | 2003-160540 A | 6/2003 |
| JP | 2005-208414 A | 8/2005 |
| JP | 2005-208415 A | 8/2005 |
| JP | 2005-208416 A | 8/2005 |
| JP | 2005-289980 A | 10/2005 |
| JP | 2006-330710 A | 12/2006 |
| JP | 2009-179563 A | 8/2009 |
| JP | 2010-031223 A | 2/2010 |
| JP | 2010-105940 A | 5/2010 |

(Continued)

OTHER PUBLICATIONS

English translation of WO2014132978. (Year: 2014).*

(Continued)

*Primary Examiner* — Chanceity N Robinson
*Assistant Examiner* — Anna Malloy
(74) *Attorney, Agent, or Firm* — Birch, Stewart, Kolasch & Birch, LLP

(57) ABSTRACT

A polymerizable compound, a polymerizable composition, and a polymer, which have a low melting point at a practical level and exhibit excellent solubility in a general-purpose solvent, can be produced at low cost. The polymerizable compound, polymerizable composition, and polymer can produce an optical film, which exhibits excellent transparency and achieves uniform conversion of polarized light over a wide wavelength band, and an optically anisotropic article. The polymerizable compound is represented by formula (I).

(I)

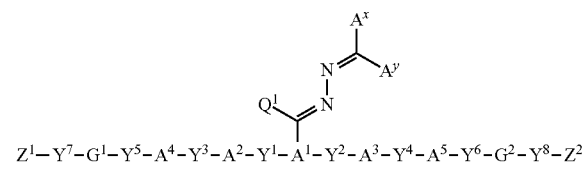

20 Claims, No Drawings

(56) References Cited

FOREIGN PATENT DOCUMENTS

| JP | 2010-537954 A | 12/2010 | | |
|----|---------------|---------|---|---|
| JP | 2010-537955 A | 12/2010 | | |
| JP | 2011-006360 A | 1/2011 | | |
| JP | 2011-006361 A | 1/2011 | | |
| JP | 2011-042606 A | 3/2011 | | |
| WO | WO 00/26705 A1 | 5/2000 | | |
| WO | WO 2006/052001 A1 | 5/2006 | | |
| WO | WO 2012/141245 A1 | 10/2012 | | |
| WO | WO-2012141245 A1 * | 10/2012 | ............ | C09K 19/32 |
| WO | WO 2014/010325 A1 | 1/2014 | | |
| WO | WO-2014132978 A1 * | 9/2014 | ........... | G02B 5/3083 |

OTHER PUBLICATIONS

International Search Report issued in PCT/JP2014/053215, dated May 13, 2014.
Written Opinion of the International Searching Authority issued in PCT/JP2014/053215, dated Aug. 27, 2015.
Extended European Search Report for European Application No. 14751337.8, dated Oct. 18, 2016.

* cited by examiner

POLYMERIZABLE COMPOUND, POLYMERIZABLE COMPOSITION, POLYMER, AND OPTICALLY ANISOTROPIC BODY

TECHNICAL FIELD

The present invention relates to a polymerizable compound, a polymerizable composition, and a polymer that can produce an optical film that achieves uniform conversion of polarized light over a wide wavelength band, and also relates to an optically anisotropic article.

BACKGROUND ART

A quarter-wave plate that converts linearly polarized light into circularly polarized light, a half-wave plate that changes the plane of vibration of linearly polarized light by 90°, and the like are known. These retardation films can achieve accurate conversion of specific monochromatic light so that $\frac{1}{4}\lambda$ or $\frac{1}{2}\lambda$ retardation occurs.

However, known retardation films have a problem in that polarized light that passes through is converted into colored polarized light. Specifically, since a material that forms the retardation film has wavelength dispersion with respect to retardation, and a polarization state distribution corresponding to each wavelength occurs with respect to white light that includes different light rays in the visible region, it is impossible to achieve accurate $\frac{1}{4}\lambda$ or $\frac{1}{2}\lambda$ retardation over the entire wavelength band.

In order to solve the above problem, various wideband retardation films that can achieve uniform retardation with respect to light over a wide wavelength band (i.e., retardation films having reverse wavelength dispersion) have been studied (see Patent Documents 1 to 6, for example).

It has been desired to reduce the thickness of a flat panel display as much as possible along with an improvement in performance and widespread use of mobile information terminals (e.g., mobile personal computers and mobile phones). Therefore, a reduction in thickness of the retardation film has also been desired.

It has been considered that it is most effective to produce a retardation film by applying a polymerizable composition that includes a low-molecular-weight polymerizable compound to a film substrate in order to reduce the thickness of the retardation film. Various low-molecular-weight polymerizable compounds having excellent wavelength dispersion, and various polymerizable compositions using such polymerizable compounds have been developed (see Patent Documents 7 to 24, for example).

However, the low-molecular-weight polymerizable compounds or the polymerizable compositions disclosed in Patent Documents 7 to 24 have a number of problems in that reverse wavelength dispersion may be insufficient, or it may be difficult to apply the low-molecular-weight polymerizable compounds or the polymerizable compositions to a film due to a high melting point that is not suitable for an industrial process, or the temperature range in which liquid crystallinity is obtained may be very narrow, or solubility in a solvent generally used for an industrial process may be low. Moreover, since these low-molecular-weight polymerizable compounds and the like are synthesized by performing a plurality of steps using a synthesis method that utilizes an expensive reagent, the production cost increases.

Patent Document 25 proposes a compound (azine compound) that includes an azine linkage and has reverse wavelength dispersion in order to solve these problems.

RELATED-ART DOCUMENT

Patent Document

Patent Document 1: JP-A-10-68816
Patent Document 2: JP-A-10-90521
Patent Document 3: JP-A-11-52131
Patent Document 4: JP-A-2000-284126 (US20020159005A1)
Patent Document 5: JP-A-2001-4837
Patent Document 6: WO2000/026705
Patent Document 7: JP-A-2002-267838
Patent Document 8: JP-A-2003-160540 (US20030102458A1)
Patent Document 9: JP-A-2005-208414
Patent Document 10: JP-A-2005-208415
Patent Document 11: JP-A-2005-208416
Patent Document 12: JP-A-2005-289980 (US20070176145A1)
Patent Document 13: JP-A-2006-330710 (US20090072194A1)
Patent Document 14: JP-A-2009-179563 (US20090189120A1)
Patent Document 15: JP-A-2010-31223
Patent Document 16: JP-A-2011-6360
Patent Document 17: JP-A-2011-6361
Patent Document 18: JP-A-2011-42606
Patent Document 19: JP-T-2010-537954 (US20100201920A1)
Patent Document 20: JP-T-2010-537955 (US20100301271A1)
Patent Document 21: WO2006/052001 (US20070298191A1)
Patent Document 22: U.S. Pat. No. 6,139,771
Patent Document 23: U.S. Pat. No. 6,203,724
Patent Document 24: U.S. Pat. No. 5,567,349
Patent Document 25: WO2012/141245

SUMMARY OF THE INVENTION

Technical Problem

The azine compound disclosed in Patent Document 25 has a low melting point at a practical level, exhibits excellent solubility in a general-purpose solvent, and can be produced at low cost.

However, since the azine compound disclosed in Patent Document 25 is a yellow compound, the azine compound disclosed in Patent Document 25 is not suitable for producing an optical film used for a display device.

The invention was conceived in view of the above problems. An object of the invention is to provide a polymerizable compound, a polymerizable composition, and a polymer that have a low melting point at a practical level, exhibit excellent solubility in a general-purpose solvent (i.e., can be easily formed (molded)), can be produced at low cost, and can produce an optical film that exhibits excellent transparency (i.e., exhibits excellent light transmittance within a wavelength band of 400 to 450 nm that may vary depending on coloration), and achieves uniform conversion of polarized light over a wide wavelength band, and an optically anisotropic article.

Solution to Problem

The inventors of the invention conducted extensive studies in order to solve the above problem. As a result, the inventors found that an optical film that achieves uniform conversion of polarized light over a wide wavelength band, and exhibits satisfactory performance (e.g., transparency), can be produced at low cost by utilizing an optically anisotropic article produced using a polymer that is obtained by polymerizing a polymerizable compound represented by the following formula (I), or polymerizing a polymerizable composition that includes the polymerizable compound and an initiator. This finding has led to the completion of the invention.

Several aspects of the invention provide the following polymerizable compound (see (1) to (7)), polymerizable composition (see (8) and (9)), polymer (see (10) and (11)), and optically anisotropic article (see (12)).

(1) A polymerizable compound represented by the following formula (I),

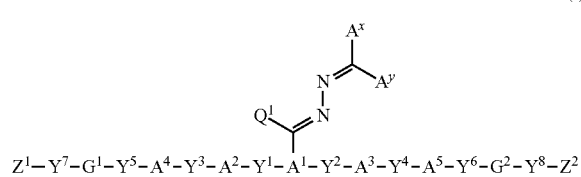

$$Z^1-Y^7-G^1-Y^5-A^4-Y^3-A^2-Y^1-A^1-Y^2-A^3-Y^4-A^5-Y^6-G^2-Y^8-Z^2$$

wherein $Y^1$ to $Y^8$ are independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—, $R^1$ is a hydrogen atom or an alkyl group having 1 to 6 carbon atoms, $G^1$ and $G^2$ are independently a substituted or unsubstituted divalent linear aliphatic group having 1 to 20 carbon atoms that optionally includes —O—, —S—, —O—C(=O)—, —C(=O)—O—, —O—C(=O)—O—, —NR$^2$—C(=O)—, —C(=O)—NR$^2$—, —NR$^2$—, or —C(=O)—, provided that the case where the aliphatic group includes two or more contiguous —O— or —S— is excluded, $R^2$ is a hydrogen atom or an alkyl group having 1 to 6 carbon atoms, $Z^1$ and $Z^2$ are independently an alkenyl group having 2 to 10 carbon atoms that is substituted with a halogen atom, or unsubstituted, $A^x$ is an organic group having 2 to 30 carbon atoms that includes at least one aromatic ring selected from the group consisting of an aromatic hydrocarbon ring and a heteroaromatic ring, $A^y$ is a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, —C(=O)—R$^3$, —SO$_2$—R$^4$, or an organic group having 2 to 30 carbon atoms that includes at least one aromatic ring selected from the group consisting of an aromatic hydrocarbon ring and a heteroaromatic ring, provided that the aromatic ring included in $A^x$ and the aromatic ring optionally included in $A^y$ are either substituted or unsubstituted, and $A^x$ and $A^y$ are optionally bonded to each other to form a ring, $R^3$ is a substituted or unsubstituted alkyl group having 1 to 12 carbon atoms, a substituted or unsubstituted alkenyl group having 2 to 12 carbon atoms, or a substituted or unsubstituted cycloalkyl group having 3 to 12 carbon atoms, $R^4$ is an alkyl group having 1 to 12 carbon atoms, an alkenyl group having 2 to 12 carbon atoms, a phenyl group, or a 4-methylphenyl group, $A^1$ is a substituted or unsubstituted trivalent aromatic group, $A^2$ and $A^3$ are independently a substituted or unsubstituted divalent alicyclic hydrocarbon group having 3 to 30 carbon atoms, $A^4$ and $A^5$ are independently a substituted or unsubstituted divalent aromatic group having 6 to 30 carbon atoms, and $Q^1$ is a hydrogen atom, or a substituted or unsubstituted alkyl group having 1 to 6 carbon atoms.

(2) The polymerizable compound according to (1), wherein the total number of π electrons included in $A^x$ and $A^y$ is 4 to 24.

(3) The polymerizable compound according to (1), wherein $A^1$ is a substituted or unsubstituted trivalent benzene ring group, or a substituted or unsubstituted trivalent naphthalene ring group.

(4) The polymerizable compound according to (1), wherein $Y^1$ to $Y^8$ are independently a chemical single bond, —O—, —O—C(=O)—, —C(=O)—O—, or —O—C(=O)—O—.

(5) The polymerizable compound according to (1), wherein $Z^1$ and $Z^2$ are independently CH$_2$=CH—, CH$_2$=C(CH$_3$)—, or CH$_2$=C(Cl)—.

(6) The polymerizable compound according to (1), wherein $G^1$ and $G^2$ are independently a substituted or unsubstituted divalent aliphatic group having 1 to 20 carbon atoms that optionally includes —O—, —O—C(=O)—, —C(=O)—O—, or —C(=O)—, provided that the case where the aliphatic group includes two or more contiguous —O— is excluded.

(7) The polymerizable compound according to (1), wherein $G^1$ and $G^2$ are independently an alkylene group having 1 to 12 carbon atoms.

(8) A polymerizable composition including at least one type of the polymerizable compound according to any one of (1) to (7).

(9) A polymerizable composition including at least one type of the polymerizable compound according to any one of (1) to (7), and an initiator.

(10) A polymer obtained by polymerizing the polymerizable compound according to any one of (1) to (7), or polymerizing the polymerizable composition according to (8) or (9).

(11) The polymer according to (10), the polymer being a liquid crystalline polymer.

(12) An optically anisotropic article including the polymer according to (11).

Advantageous Effects of the Invention

The polymerizable compound according to one aspect of the invention has a low melting point at a practical level, exhibits excellent solubility in a general-purpose solvent (i.e., can be easily formed (molded)), can be produced at low cost, and can produce an optical film that exhibits excellent transparency (i.e., exhibits excellent light transmittance within a wavelength band of 400 to 450 nm that may vary depending on coloration), and achieves uniform conversion of polarized light over a wide wavelength band.

The polymerizable composition according to one aspect of the invention and the polymer according to one aspect of the invention make it possible to inexpensively obtain an optically anisotropic article that achieves uniform conversion of polarized light over a wide wavelength band, and exhibits satisfactory performance (e.g., transparency).

Since the optically anisotropic article according to one aspect of the invention is produced using the polymer according to one aspect of the invention, the optically anisotropic article can be produced at low cost, achieves uniform conversion of polarized light over a wide wavelength band, and exhibits satisfactory performance (e.g., transparency).

An antireflective film may be produced by combining the optically anisotropic article according to one aspect of the invention that is formed in the shape of a film with a polarizer. The antireflective film may suitably be used to prevent reflection from a touch panel, an organic electroluminescence device, and the like.

DESCRIPTION OF EMBODIMENTS

A polymerizable compound, a polymerizable composition, a polymer, and an optically anisotropic article according to the exemplary embodiments of the invention are described in detail below.

1) Polymerizable Compound

A polymerizable compound according to one embodiment of the invention is a compound represented by the formula (I).

$Y^1$ to $Y^8$ in the formula (I) are independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—.

$R^1$ is a hydrogen atom or an alkyl group having 1 to 6 carbon atoms.

Examples of the alkyl group having 1 to 6 carbon atoms that may be represented by $R^1$ include a methyl group, an ethyl group, an n-propyl group, an isopropyl group, an n-butyl group, a sec-butyl group, a t-butyl group, an n-pentyl group, an n-hexyl group, and the like.

$R^1$ is preferably a hydrogen atom or an alkyl group having 1 to 4 carbon atoms.

It is preferable that $Y^1$ to $Y^8$ included in the polymerizable compound according to one embodiment of the invention be independently a chemical single bond, —O—, —O—C(=O)—, —C(=O)—O—, or —O—C(=O)—O—.

$G^1$ and $G^2$ are independently a substituted or unsubstituted divalent aliphatic group having 1 to 20 carbon atoms.

Examples of the divalent aliphatic group having 1 to 20 carbon atoms include an alkylene group having 1 to 20 carbon atoms, such as a methylene group, an ethylene group, a propylene group, a butylene group, a pentylene group, and a hexylene group; a divalent aliphatic group having a linear structure, such as an alkenylene group having 2 to 20 carbon atoms (e.g., ethenylene group, propenylene group, butenylene group, and pentenylene group); a cycloalkanediyl group having 3 to 20 carbon atoms, such as
a cyclopropane-1,1-diyl group, a cyclopropane-1,2-diyl group, a cyclobutane-1,1-diyl group, a cyclobutane-1,2-diyl group, a cyclopentane-1,1-diyl group,
a cyclopentane-1,2-diyl group, a cyclohexane-1,1-diyl group, a cyclohexane-1,2-diyl group, a cycloheptane-1,1-diyl group, a cycloheptane-1,2-diyl group,
a cyclooctane-1,1-diyl group, a cyclooctane-1,2-diyl group, a cyclononane-1,1-diyl group, a cyclononane-1,2-diyl group, a cyclodecane-1,1-diyl group, and
a cyclodecane-1,2-diyl group; a cycloalkenediyl group having 4 to 20 carbon atoms, such as a 2-cyclobutene-1,1-diyl group, a 1-cyclobutene-1,2-diyl group,
a 2-cyclobutene-1,2-diyl group, a 2-cyclopentene-1,1-diyl group,
a 1-cyclopentene-1,2-diyl group, a 2-cyclohexene-1,1-diyl group,
a 1-cyclohexene-1,2-diyl group, a 2-cycloheptene-1,1-diyl group,
a 1-cycloheptene-1,2-diyl group, a 2-cyclooctene-1,1-diyl group,
a 1-cyclooctene-1,2-diyl group, a 2-cyclononene-1,1-diyl group,
a 1-cyclononene-1,2-diyl group, a 2-cyclodecene-1,1-diyl group, and
a 1-cyclodecene-1,2-diyl group; a divalent aliphatic group such as a divalent fused alicyclic group having 10 to 30 carbon atoms (e.g., divalent adamantane ring group and divalent norbornene ring group); and the like.

Examples of a substituent that may substitute the divalent aliphatic group represented by $G^1$ and $G^2$ include halogen atoms such as a fluorine atom, a chlorine atom, a bromine atom, and an iodine atom; alkoxy groups having 1 to 6 carbon atoms, such as a methoxy group, an ethoxy group, an n-propoxy group, an isopropoxy group, an n-butoxy group, a sec-butoxy group, a t-butoxy group, an n-pentyloxy group, and an n-hexyloxy group; and the like. Among these, a fluorine atom, a methoxy group, and an ethoxy group are preferable.

The aliphatic group optionally includes —O—, —S—, —O—C(=O)—, —C(=O)—O—, —O—C(=O)—O—, —NR$^2$—C(=O)—, —C(=O)—NR$^2$—, —NR$^2$—, or —C(=O)— (provided that a case where the aliphatic group includes two or more contiguous —O— or —S— is excluded). $R^2$ is a hydrogen atom or an alkyl group having 1 to 6 carbon atoms similar to that represented by $R^1$, and is preferably a hydrogen atom or a methyl group.

—O—, —O—C(=O)—, —C(=O)—O—, and —C(=O)— are preferable as the group that is optionally included in the aliphatic group.

Specific examples of the aliphatic group that includes the above group include —CH$_2$—CH$_2$—O—CH$_2$—CH$_2$—, —CH$_2$—CH$_2$—S—CH$_2$—CH$_2$—, —CH$_2$—CH$_2$—O—C(=O)—CH$_2$—CH$_2$—, —CH$_2$—CH$_2$—C(=O)—O—CH$_2$—CH$_2$—, —CH$_2$—CH$_2$—C(=O)—O—CH$_2$—, —CH$_2$—O—C(=O)—O—CH$_2$—CH$_2$—, —CH$_2$—CH$_2$—NR$^2$—C(=O)—CH$_2$—CH$_2$—, —CH$_2$—CH$_2$—C(=O)—NR$^2$—CH$_2$—, —CH$_2$—NR$^2$—CH$_2$—CH$_2$—, —CH$_2$—C(=O)—CH$_2$—, and the like.

It is preferable that $G^1$ and $G^2$ be independently a divalent aliphatic group having a linear structure (e.g., an alkylene group having 1 to 20 carbon atoms or an alkenylene group having 2 to 20 carbon atoms), more preferably an alkylene group having 1 to 12 carbon atoms (e.g., methylene group, ethylene group, trimethylene group, propylene group, tetramethylene group, pentamethylene group, hexamethylene group, or octamethylene group), and particularly preferably a tetramethylene group (—(CH$_2$)$_4$—) or a hexamethylene group (—(CH$_2$)$_6$—), in order to ensure that the intended effects of the invention can be more advantageously achieved.

$Z^1$ and $Z^2$ are independently an alkenyl group having 2 to 10 carbon atoms that is substituted with a halogen atom, or unsubstituted.

The number of carbon atoms of the alkenyl group is preferably 2 to 6. Examples of the halogen atom that may substitute the alkenyl group represented by $Z^1$ and $Z^2$ include a fluorine atom, a chlorine atom, a bromine atom, and the like. Among these, a chlorine atom is preferable.

Specific examples of the alkenyl group having 2 to 10 carbon atoms represented by $Z^1$ and $Z^2$ include $CH_2=CH-$, $CH_2=C(CH_3)-$, $CH_2=CH-CH_2-$, $CH_3-CH=CH-$, $CH_2=CH-CH_2-CH_2-$, $CH_2=C(CH_3)-CH_2-CH_2-$, $(CH_3)_2C=CH-CH_2-$, $(CH_3)_2C=CH-CH_2-CH_2-$, $CH_2=C(Cl)-$, $CH_2=C(CH_3)-CH_2-$, $CH_3-CH=CH-CH_2-$, and the like.

It is preferable that $Z^1$ and $Z^2$ be independently $CH_2=CH-$, $CH_2=C(CH_3)-$, $CH_2=C(Cl)-$, $CH_2=CH-CH_2-$, $CH_2=C(CH_3)-CH_2-$, or $CH_2=C(CH_3)-CH_2-CH_2-$, more preferably $CH_2=CH-$, $CH_2=C(CH_3)-$, or $CH_2=C(Cl)-$, and still more preferably $CH_2=CH-$ or $CH_2=C(CH_3)-$, in order to ensure that the intended effects of the invention can be more advantageously achieved.

$A^x$ is an organic group having 2 to 30 carbon atoms that includes at least one aromatic ring selected from the group consisting of an aromatic hydrocarbon ring and a heteroaromatic ring.

The term "aromatic ring" used herein refers to a cyclic structure that exhibits aromaticity according to Huckel's rule in a broad sense (i.e., a cyclic conjugated structure that includes (4n+2) π electrons, and a structure that exhibits aromaticity in which lone pairs of heteroatoms such as sulfur or oxygen are involved in the π electron system (e.g., thiophene and furan)).

The organic group having 2 to 30 carbon atoms represented by $A^x$ that includes at least one aromatic ring selected from the group consisting of an aromatic hydrocarbon ring and a heteroaromatic ring may include a plurality of aromatic rings, and may include an aromatic hydrocarbon ring and a heteroaromatic ring.

Examples of the aromatic hydrocarbon ring include a benzene ring, a naphthalene ring, an anthracene ring, a fluorene ring, and the like. Examples of the heteroaromatic ring include a 5-membered heteroaromatic ring such as a pyrrole ring, a furan ring, a thiophene ring, a pyrazole ring, an imidazole ring, an oxazole ring, and a thiazole ring; a 6-membered heteroaromatic ring such as a pyridine ring, a pyridazine ring, a pyrimidine ring, and a pyrazine ring; a fused heteroaromatic ring such as a benzimidazole ring, a benzothiophene ring, a benzoxazole ring, a benzothiazole ring, and a carbazole ring; and the like.

The aromatic ring included in $A^x$ may be substituted with a substituent at an arbitrary position. Examples of the substituent include a halogen atom such as a fluorine atom and a chlorine atom; a cyano group; an alkyl group having 1 to 6 carbon atoms, such as a methyl group, an ethyl group, and a propyl group; an alkenyl group having 2 to 6 carbon atoms, such as a vinyl group and an allyl group; an alkyl halide group having 1 to 6 carbon atoms, such as a trifluoromethyl group; a substituted amino group; an alkoxy group having 1 to 6 carbon atoms, such as a methoxy group, an ethoxy group, and an isopropoxy group; a nitro group; an aryl group such as a phenyl group and a naphthyl group; a $-C(=O)-OR$ group; an $-SO_2R$ group; and the like. R is an alkyl group having 1 to 6 carbon atoms (e.g., methyl group or ethyl group) or an aryl group having 6 to 14 carbon atoms (e.g., phenyl group, 1-naphthyl group, or 2-naphthyl group).

The aromatic ring included in $A^x$ may be substituted with a plurality of identical or different substituents, and two adjacent substituents may be bonded to each other to form a ring. The ring formed by two adjacent substituents may be either a monocyclic ring or a fused polycyclic ring.

Note that the number of carbon atoms (i.e., 2 to 30) of the organic group represented by $A^x$ refers to the total number of carbon atoms of the organic group excluding the number of carbon atoms of a substituent. This also applies to the number of carbon atoms of the organic group that may be represented by $A^y$.

Examples of the organic group having 2 to 30 carbon atoms represented by $A^x$ that includes at least one aromatic ring selected from the group consisting of an aromatic hydrocarbon ring and a heteroaromatic ring include an aromatic hydrocarbon ring group; a heteroaromatic ring group; an alkyl group having 3 to 30 carbon atoms that includes at least one aromatic ring selected from the group consisting of an aromatic hydrocarbon ring and a heteroaromatic ring; an alkenyl group having 4 to 30 carbon atoms that includes at least one aromatic ring selected from the group consisting of an aromatic hydrocarbon ring and a heteroaromatic ring; an alkynyl group having 4 to 30 carbon atoms that includes at least one aromatic ring selected from the group consisting of an aromatic hydrocarbon ring and a heteroaromatic ring; and the like.

$A^y$ is a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, $-C(=O)-R^3$, $-SO_2-R^4$, or an organic group having 2 to 30 carbon atoms that includes at least one aromatic ring selected from the group consisting of an aromatic hydrocarbon ring and a heteroaromatic ring. $R^3$ is a substituted or unsubstituted alkyl group having 1 to 12 carbon atoms, a substituted or unsubstituted alkenyl group having 2 to 12 carbon atoms, or a substituted or unsubstituted cycloalkyl group having 3 to 12 carbon atoms, and $R^4$ is an alkyl group having 1 to 12 carbon atoms, an alkenyl group having 2 to 12 carbon atoms, a phenyl group, or a 4-methylphenyl group.

Examples of the alkyl group having 1 to 20 carbon atoms (that is substituted or unsubstituted) that may be represented by $A^y$ include a methyl group, an ethyl group, an n-propyl group, an isopropyl group, an n-butyl group, a sec-butyl group, a t-butyl group, an n-pentyl group, an isopentyl group, a neopentyl group, an n-hexyl group, an isohexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-icosyl group, and the like. The number of carbon atoms of the substituted or unsubstituted alkyl group having 1 to 20 carbon atoms is preferably 1 to 12, and more preferably 1 to 6.

Examples of the alkenyl group having 2 to 20 carbon atoms (that is substituted or unsubstituted) that may be represented by $A^y$ include a vinyl group, a propenyl group, an isopropenyl group, a butenyl group, a pentenyl group, a hexenyl group, a heptenyl group, an octenyl group, a decenyl group, an undecenyl group, a dodecenyl group, a tridecenyl group, a tetradecenyl group, a pentadecenyl group, a hexadecenyl group, a heptadecenyl group, an octadecenyl group, a nonadecenyl group, an icosenyl group, and the like.

The number of carbon atoms of the substituted or unsubstituted alkenyl group having 2 to 20 carbon atoms is preferably 2 to 12.

Examples of the cycloalkyl group having 3 to 12 carbon atoms (that is substituted or unsubstituted) that may be represented by $A^y$ include a cyclopropyl group, a cyclobutyl group, a cyclopentyl group, a cyclohexyl group, a cyclooctyl group, and the like.

Examples of a substituent that may substitute the alkyl group having 1 to 20 carbon atoms and the alkenyl group having 2 to 20 carbon atoms that may be represented by $A^y$ include a halogen atom such as a fluorine atom and a chlorine atom; a cyano group; a substituted amino group such as a dimethylamino group; an alkoxy group having 1 to 6 carbon atoms, such as a methoxy group, an ethoxy group, and an isopropoxy group; an alkoxy group having 1 to 6 carbon atoms that is substituted with an alkoxy group having 1 to 6 carbon atoms, such as a methoxymethoxy group and a methoxyethoxy group; a nitro group; an aryl group such as a phenyl group and a naphthyl group; a cycloalkyl group having 3 to 8 carbon atoms, such as a cyclopropyl group, a cyclopentyl group, and a cyclohexyl group; —C(=O)—$R^5$; —C(=O)—$OR^5$; —$SO_2R^6$; a hydroxyl group; and the like. $R^5$ is a substituted or unsubstituted alkyl group having 1 to 12 carbon atoms, a substituted or unsubstituted alkenyl group having 2 to 12 carbon atoms, or a substituted or unsubstituted cycloalkyl group having 3 to 12 carbon atoms (similar to those that may be represented by $R^3$), and $R^6$ is an alkyl group having 1 to 12 carbon atoms, an alkenyl group having 2 to 12 carbon atoms, a phenyl group, or a 4-methylphenyl group (similar to those that may be represented by $R^4$).

Examples of a substituent that may substitute the cycloalkyl group having 3 to 12 carbon atoms that may be represented by $A^y$ include a halogen atom such as a fluorine atom and a chlorine atom; a cyano group; a substituted amino group such as a dimethylamino group; an alkyl group having 1 to 6 carbon atoms, such as a methyl group, an ethyl group, and a propyl group; an alkoxy group having 1 to 6 carbon atoms, such as a methoxy group, an ethoxy group, and an isopropoxy group; a nitro group; an aryl group such as a phenyl group and a naphthyl group; a cycloalkyl group having 3 to 8 carbon atoms, such as a cyclopropyl group, a cyclopentyl group, and a cyclohexyl group; —C(=O)—$R^5$; —C(=O)—$OR^5$; —$SO_2R^6$; a hydroxyl group; and the like. Note that $R^5$ and $R^6$ are the same as defined above.

Examples of the alkyl group having 1 to 12 carbon atoms (that is substituted or unsubstituted) that may be represented by $R^3$ included in —C(=O)—$R^3$, include a methyl group, an ethyl group, an n-propyl group, an isopropyl group, an n-butyl group, a sec-butyl group, a t-butyl group, an n-pentyl group, an isopentyl group, an n-hexyl group, an n-octyl group, an n-decyl group, an n-dodecyl group, and the like.

Examples of the alkenyl group having 2 to 12 carbon atoms (that is substituted or unsubstituted) that may be represented by $R^3$, include a vinyl group, a propenyl group, a butenyl group, a pentenyl group, a hexenyl group, an octenyl group, a decenyl group, a dodecenyl group, and the like.

Examples of a substituent that may substitute the alkyl group having 1 to 12 carbon atoms and the alkenyl group having 2 to 12 carbon atoms include those mentioned above in connection with the alkyl group having 1 to 20 carbon atoms and the alkenyl group having 2 to 20 carbon atoms that may be represented by A.

Examples of the cycloalkyl group having 3 to 12 carbon atoms (that is substituted or unsubstituted) that may be represented by $R^3$, include those mentioned above in connection with $A^y$.

Examples of the alkyl group having 1 to 12 carbon atoms and the alkenyl group having 2 to 12 carbon atoms that may be represented by $R^4$ included in —$SO_2$—$R^4$, include those mentioned above in connection with the alkyl group having 1 to 12 carbon atoms and the alkenyl group having 2 to 12 carbon atoms that may be represented by $R^3$.

Examples of the organic group having 2 to 30 carbon atoms that may be represented by $A^y$ that includes at least one aromatic ring selected from the group consisting of an aromatic hydrocarbon ring and a heteroaromatic ring, include those mentioned above in connection with $A^x$.

$A^y$ is preferably a hydrogen atom, a substituted or unsubstituted alkyl group having 1 to 12 carbon atoms, a substituted or unsubstituted alkenyl group having 2 to 12 carbon atoms, a substituted or unsubstituted cycloalkyl group having 3 to 12 carbon atoms, —C(=O)—$R^3$, —$SO_2$—$R^4$, or an organic group having 2 to 30 carbon atoms that includes at least one aromatic ring selected from the group consisting of an aromatic hydrocarbon ring and a heteroaromatic ring. Note that $R^3$ and $R^4$ are the same as defined above.

$A^x$ and $A^y$ are optionally bonded to each other to form a ring. Examples of such a ring include a substituted or unsubstituted unsaturated heterocyclic ring having 4 to 30 carbon atoms, and a substituted or unsubstituted unsaturated carbocyclic ring having 6 to 30 carbon atoms.

Specific examples of the organic group having 2 to 30 carbon atoms represented by $A^x$ and $A^y$ that includes at least one aromatic ring selected from the group consisting of an aromatic hydrocarbon ring and a heteroaromatic ring, include the groups respectively represented by the following formulas. Note that the organic group is not limited to the groups respectively represented by the following formulas. "—" in the following formulas is the bonding position of the aromatic ring (hereinafter the same).

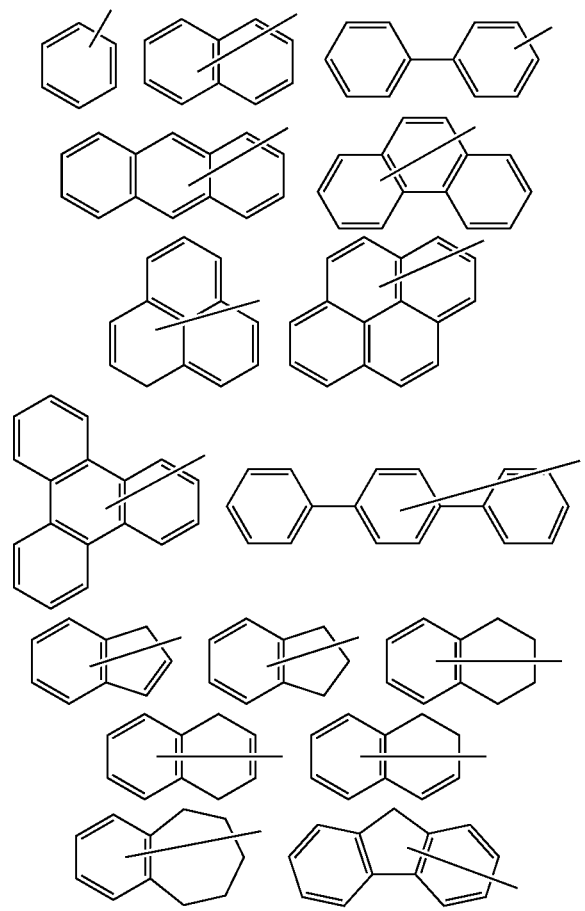

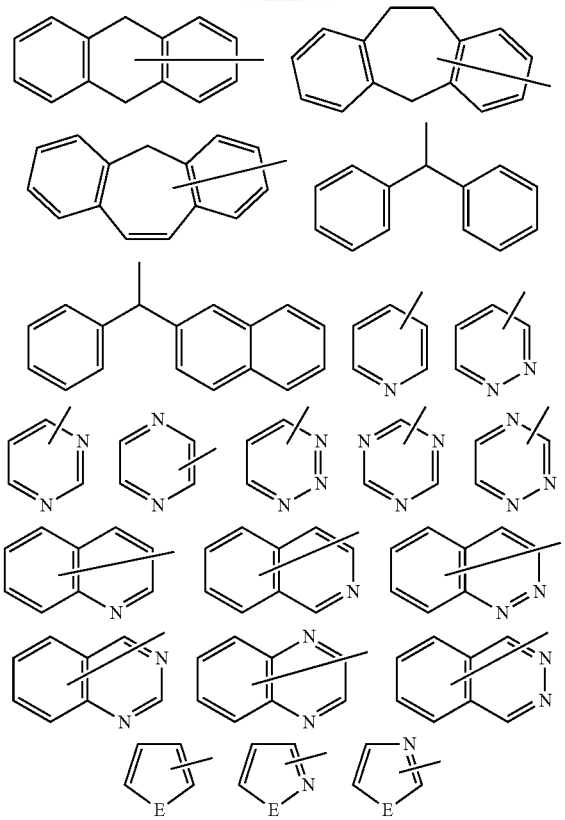

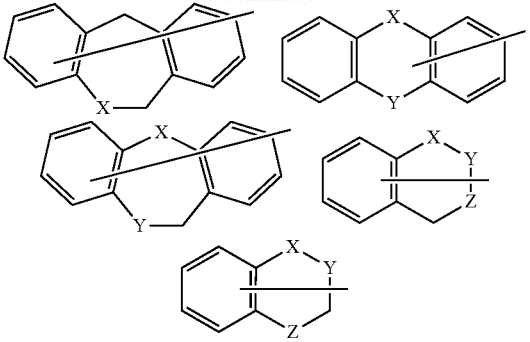

wherein X, Y, and Z are independently NR[7], an oxygen atom, a sulfur atom, —SO—, or —SO$_2$—, provided that the case where two or more oxygen atoms, sulfur atoms, —SO—, or —SO$_2$— are situated at adjacent positions is excluded, and R[7] is the same as defined above.

Among these, the following groups are preferable.

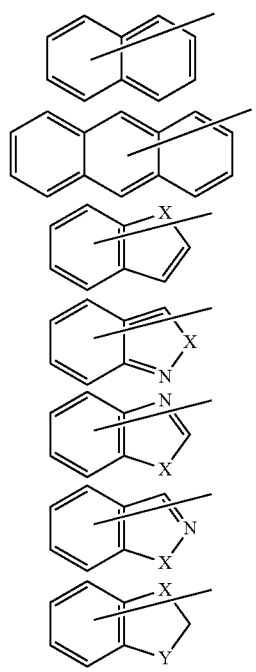

wherein E is NR[7], an oxygen atom, or a sulfur atom, and R[7] is a hydrogen atom, or an alkyl group having 1 to 6 carbon atoms (e.g., methyl group or ethyl group).

The following groups are particularly preferable.

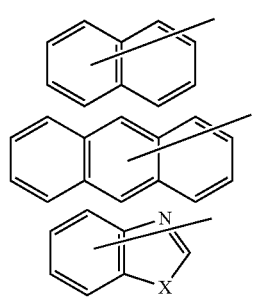

A$^x$ and A$^y$ are optionally bonded to each other to form a ring. In this case, it is preferable that A$^x$ and A$^y$ form a substituted or unsubstituted unsaturated heterocyclic ring having 4 to 30 carbon atoms, or a substituted or unsubstituted unsaturated carbocyclic ring having 6 to 30 carbon atoms.

The unsaturated heterocyclic ring having 4 to 30 carbon atoms and the unsaturated carbocyclic ring having 6 to 30 carbon atoms are not particularly limited, and may or may not exhibit aromaticity. The rings respectively represented by the following formulas are preferable as the unsaturated heterocyclic ring having 4 to 30 carbon atoms and the unsaturated carbocyclic ring having 6 to 30 carbon atoms. Note that a double bond that links the ring and the nitrogen atom is also shown in the following formulas for convenience (hereinafter the same).

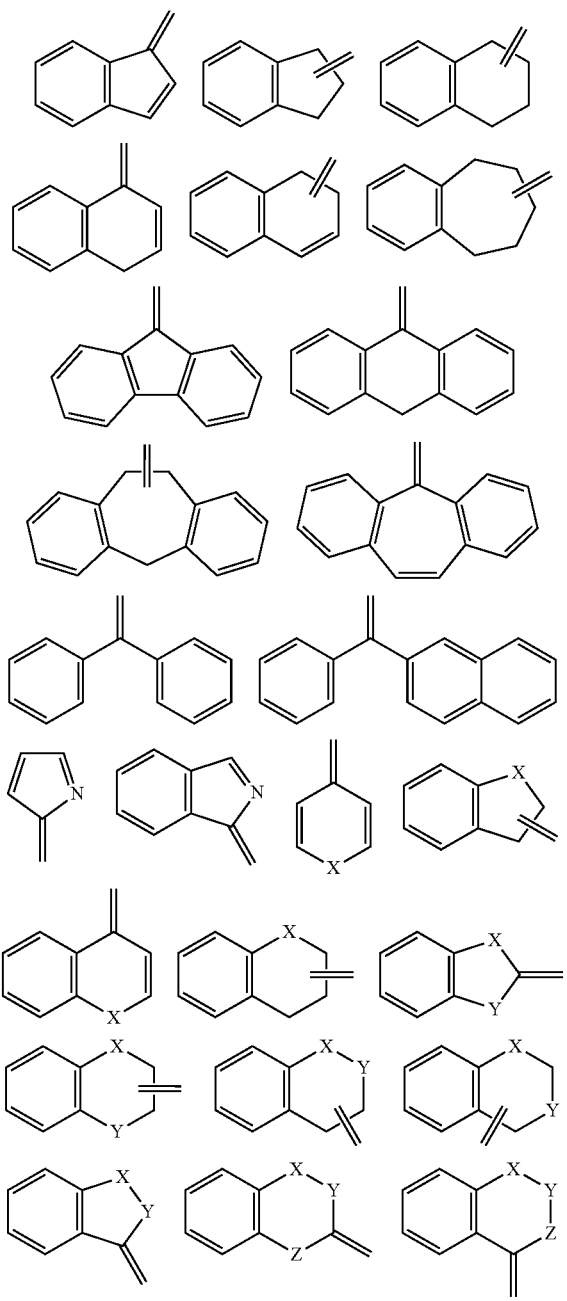

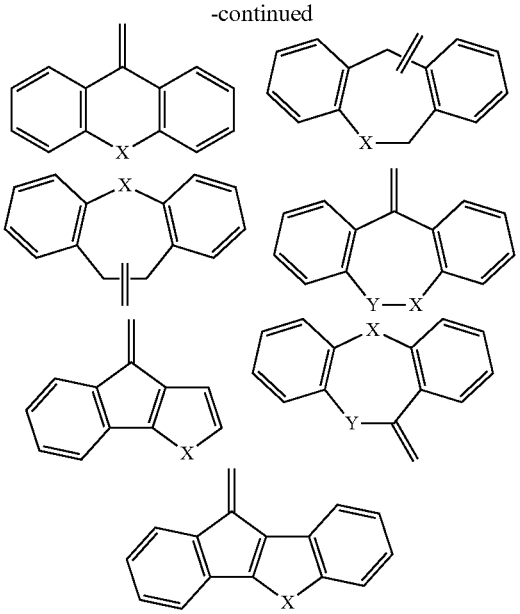

wherein X, Y, and Z are the same as defined above.

These rings may be substituted with a substituent.

Examples of the substituent include a halogen atom, a cyano group, an alkyl group having 1 to 6 carbon atoms, an alkoxy group having 1 to 6 carbon atoms, a nitro group, a —C(=O)—OR group, an —SO$_2$R group, and the like. Note that R is the same as defined above.

It is particularly preferable that $A^x$ and $A^y$ form a ring among the rings respectively represented by the following formulas when $A^x$ and $A^y$ are bonded to each other to form a ring.

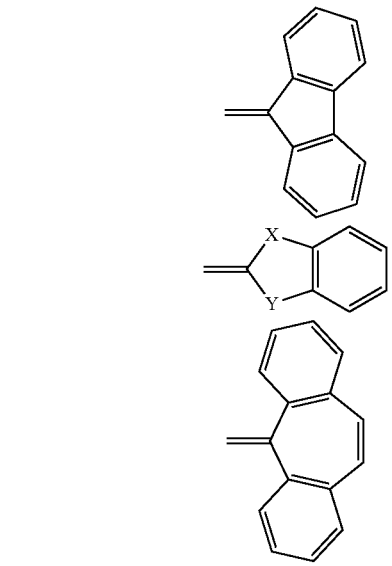

wherein X and Y are the same as defined above. It is preferable that X and Y be a sulfur atom and NR$^7$ (wherein R$^7$ is the same as defined above), respectively.

The total number of π electrons included in $A^x$ and $A^y$ is preferably 4 to 24 in order to ensure that the intended effects of the invention can be more advantageously achieved.

It is preferable that $A^x$ be an aromatic group having 4 to 30 carbon atoms, and $A^y$ be a hydrogen atom or a substituted or unsubstituted alkyl group, or $A^x$ and $A^y$ be bonded to each other to form an unsaturated heterocyclic ring or an unsaturated carbocyclic ring. It is more preferable that $A^x$ be a group having a structure among the structures respectively represented by the following formulas, and $A^y$ be a hydrogen atom or a substituted or unsubstituted alkyl group.

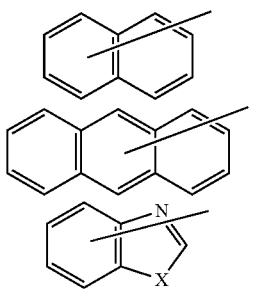

wherein X is the same as defined above.

It is still more preferable that $A^x$ and $A^y$ be bonded to each other to form a ring among the rings respectively represented by the following formulas.

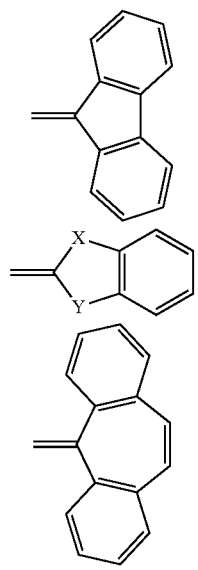

wherein X and Y are the same as defined above.

$A^1$ is a substituted or unsubstituted trivalent aromatic group. The number of carbon atoms (excluding the number of carbon atoms of a substituent) of the trivalent aromatic group represented by $A^1$ is normally 6 to 30, and preferably 6 to 15. The trivalent aromatic group may be a trivalent carbocyclic aromatic group, or may be a trivalent heterocyclic aromatic group. It is preferable that the trivalent aromatic group be a trivalent carbocyclic aromatic group, more preferably a trivalent benzene ring group or a trivalent naphthalene ring group, and still more preferably a trivalent benzene ring group or a trivalent naphthalene ring group represented by a formula among the following formulas, in order to ensure that the intended effects of the invention can be more advantageously achieved.

Note that the substituents $Y^1$ and $Y^2$ are also shown in the following formulas so that the bonding state can be easily understood ($Y^1$ and $Y^2$ are the same as defined above; hereinafter the same).

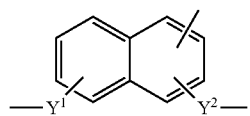

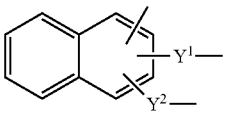

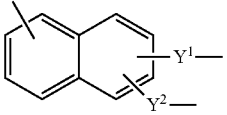

$A^1$ is more preferably a group among groups respectively represented by the following formulas (A11) to (A25), still more preferably a group among the groups respectively represented by the formulas (A11), (A13), (A15), (A19), and (A23), and particularly preferably the group represented by the formula (A11) or the group represented by the formula (A23).

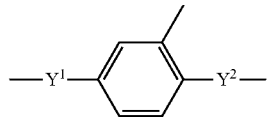
(A11)

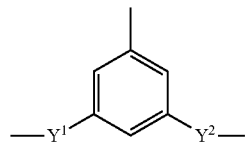
(A12)

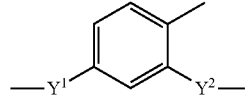
(A13)

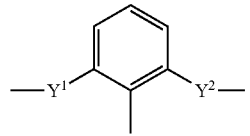
(A14)

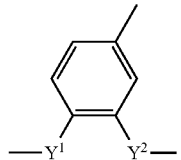
(A15)

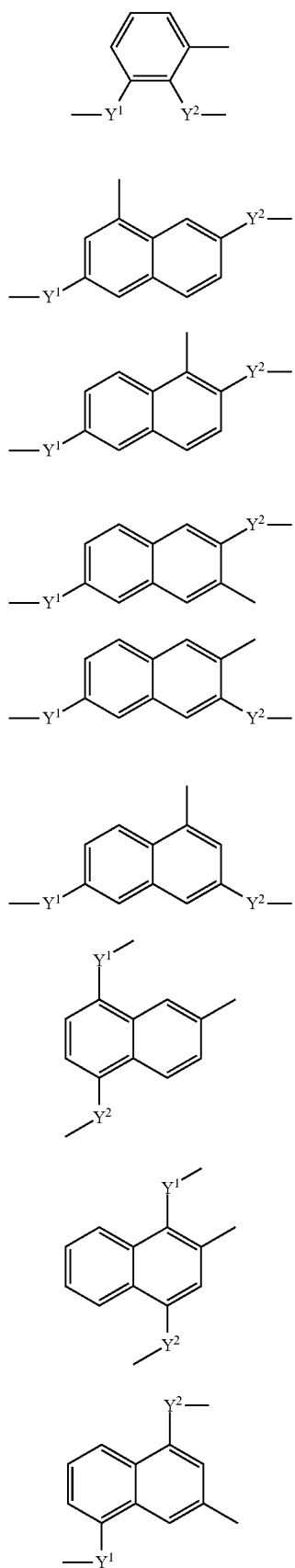

(A16)

(A17)

(A18)

(A19)

(A20)

(A21)

(A22)

(A23)

(A24)

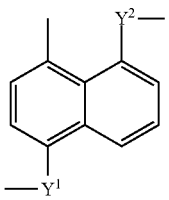

(A25)

Examples of a substituent that may substitute the trivalent aromatic group represented by $A^1$ include those mentioned above in connection with a substituent that may substitute the aromatic ring included in $A^x$. It is preferable that $A^1$ be unsubstituted.

$A^2$ and $A^3$ are independently a substituted or unsubstituted divalent alicyclic hydrocarbon group having 3 to 30 carbon atoms.

Examples of the divalent alicyclic hydrocarbon group having 3 to 30 carbon atoms include a cycloalkanediyl group having 3 to 30 carbon atoms, a divalent fused alicyclic group having 10 to 30 carbon atoms, and the like.

Examples of the cycloalkanediyl group having 3 to 30 carbon atoms include a cyclopropanediyl group; a cyclobutanediyl group such as a cyclobutane-1,2-diyl group and a cyclobutane-1,3-diyl group; a cyclopentanediyl group such as a cyclopentane-1,2-diyl group and a cyclopentane-1,3-diyl group; a cyclohexanediyl group such as a cyclohexane-1,2-diyl group, a cyclohexane-1,3-diyl group, and a cyclohexane-1,4-diyl group; a cycloheptanediyl group such as a cycloheptane-1,2-diyl group, a cycloheptane-1,3-diyl group, and a cycloheptane-1,4-diyl group;

a cyclooctanediyl group such as a cyclooctane-1,2-diyl group, a cyclooctane-1,3-diyl group, a cyclooctane-1,4-diyl group, and a cyclooctane-1,5-diyl group;

a cyclodecanediyl group such as a cyclodecane-1,2-diyl group, a cyclodecane-1,3-diyl group, a cyclodecane-1,4-diyl group, and a cyclodecane-1,5-diyl group;

a cyclododecanediyl group such as a cyclododecane-1,2-diyl group, a cyclododecane-1,3-diyl group, a cyclododecane-1,4-diyl group, and a cyclododecane-1,5-diyl group; a cyclotetradecanediyl group such as a cyclotetradecane-1,2-diyl group, a cyclotetradecane-1,3-diyl group, a cyclotetradecane-1,4-diyl group, a cyclotetradecane-1,5-diyl group, and a cyclotetradecane-1,7-diyl group; a cycloeicosanediyl group such as a cycloeicosane-1,2-diyl group and a cycloeicosane-1,10-diyl group; and the like.

Examples of the divalent fused alicyclic group having 10 to 30 carbon atoms include a decalindiyl group such as a decalin-2,5-diyl group and a decalin-2,7-diyl group; an adamantanediyl group such as an adamantane-1,2-diyl group and an adamantane-1,3-diyl group; a bicyclo[2.2.1]heptanediyl group such as a bicyclo[2.2.1]heptane-2,3-diyl group, a bicyclo[2.2.1]heptane-2,5-diyl group, and a bicyclo[2.2.1]heptane-2,6-diyl group; and the like.

These divalent alicyclic hydrocarbon groups may be substituted with a substituent at an arbitrary position.

Examples of the substituent include those mentioned above in connection with a substituent that may substitute the aromatic ring included in $A^x$.

$A^2$ and $A^3$ are preferably a divalent alicyclic hydrocarbon group having 3 to 12 carbon atoms, more preferably a cycloalkanediyl group having 3 to 12 carbon atoms, still more preferably a group among the groups respectively represented by the following formulas (A31) to (A34), and particularly preferably the group represented by the formula (A32).

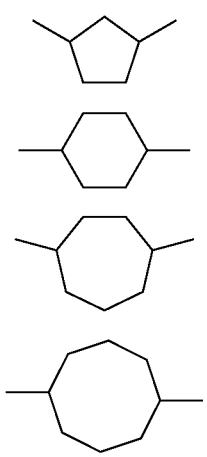

(A31)

(A32)

(A33)

(A34)

The divalent alicyclic hydrocarbon group having 3 to 30 carbon atoms is classified into a cis-stereoisomer and a trans-stereoisomer based on the difference in the steric configuration of the carbon atom bonded to $Y^1$ and $Y^3$ (or $Y^2$ and $Y^4$). For example, a cyclohexane-1,4-diyl group is classified into a cis-isomer (A32a) and a trans-isomer (A32b) (see below).

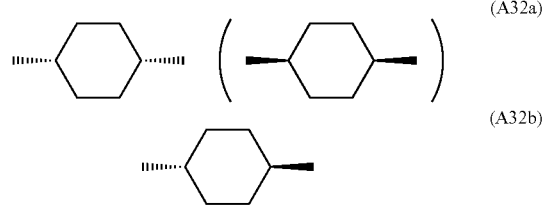

(A32a)

(A32b)

The divalent alicyclic hydrocarbon group having 3 to 30 carbon atoms may be a cis-isomer, a trans-isomer, or a mixture of a cis-isomer and a trans-isomer. Note that it is preferable that the divalent alicyclic hydrocarbon group having 3 to 30 carbon atoms be a trans-isomer or a cis-isomer, and more preferably a trans-isomer, since an excellent alignment capability can be obtained.

$A^4$ and $A^5$ are independently a substituted or unsubstituted divalent aromatic group having 6 to 30 carbon atoms.

The aromatic group represented by $A^4$ and $A^5$ may be a monocyclic aromatic group, or may be a polycyclic aromatic group.

Specific examples of a preferable aromatic group represented by $A^4$ and $A^5$ include the groups respectively represented by the following formulas.

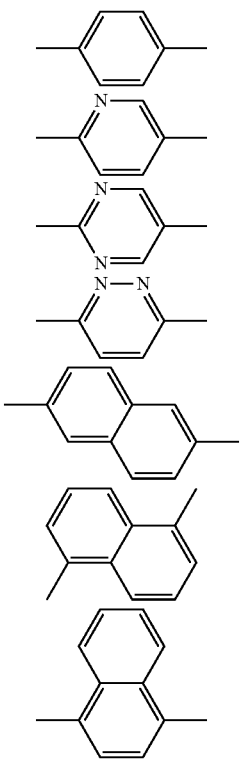

The divalent aromatic group represented by $A^4$ and $A^5$ may be substituted with a substituent at an arbitrary position. Examples of the substituent include a halogen atom, a cyano group, a hydroxyl group, an alkyl group having 1 to 6 carbon atoms, an alkoxy group having 1 to 6 carbon atoms, a nitro group, a —C(=O)—OR$^6$ group, and the like. Note that $R^6$ is an alkyl group having 1 to 6 carbon atoms. Among these, a halogen atom, an alkyl group having 1 to 6 carbon atoms, and an alkoxy group having 1 to 6 carbon atoms are preferable as the substituent. A fluorine atom is preferable as the halogen atom. A methyl group, an ethyl group, and a propyl group are preferable as the alkyl group having 1 to 6 carbon atoms. A methoxy group and an ethoxy group are preferable as the alkoxy group having 1 to 6 carbon atoms.

It is preferable that $A^4$ and $A^5$ be independently a group among the groups respectively represented by the following formula (A41), (A42), and (A43) that are optionally substituted with a substituent, and particularly preferably the group represented by the formula (A41) that is optionally substituted with a substituent, in order to ensure that the intended effects of the invention are more advantageously achieved.

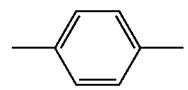

(A41)

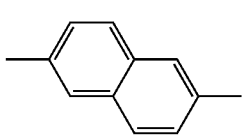

(A42)

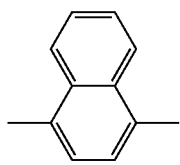

(A43)

$Q^1$ is a hydrogen atom, or a substituted or unsubstituted alkyl group having 1 to 6 carbon atoms.

Examples of the substituted or unsubstituted alkyl group having 1 to 6 carbon atoms include those mentioned above in connection with $A^x$.

$Q^1$ is preferably a hydrogen atom or an alkyl group having 1 to 6 carbon atoms, and more preferably a hydrogen atom or a methyl group.

The polymerizable compound according to one embodiment of the invention may be produced as described below, for example.

Production Method 1

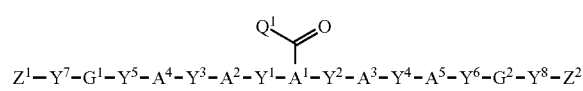

(4)

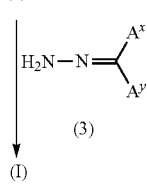

(3)

(I)

wherein $Y^1$ to $Y^8$, $G^1$, $G^2$, $Z^1$, $Z^2$, $A^x$, $A^y$, $A^1$ to $A^5$, and $Q^1$ are the same as defined above.

Specifically, the hydrazone compound represented by the formula (3) (hydrazone compound (3)) is reacted with the carbonyl compound represented by the formula (4) (carbonyl compound (4)) in a molar ratio (hydrazone compound (3):carbonyl compound (4)) of 1:2 to 2:1 (preferably 1:1.5 to 1.5:1) to produce the polymerizable compound represented by the formula (I) with high selectivity in high yield.

The above reaction may be effected in the presence of an acid catalyst such as an organic acid (e.g., (±)-10-camphorsulfonic acid or p-toluenesulfonic acid), or an inorganic acid (e.g., hydrochloric acid or sulfuric acid). The addition of the acid catalyst may reduce the reaction time, and improve the yield. The acid catalyst is normally added in an amount of 0.001 to 1 mol based on 1 mol of the carbonyl compound (4). The acid catalyst may be added directly, or a solution prepared by dissolving the acid catalyst in an appropriate solvent may be added.

A solvent used for the above reaction is not particularly limited as long as the solvent is inert to the reaction. Examples of the solvent include an alcohol-based solvent such as methyl alcohol, ethyl alcohol, n-propyl alcohol, isopropyl alcohol, n-butyl alcohol, isobutyl alcohol, sec-butyl alcohol, tert-butyl alcohol, n-pentyl alcohol, and amyl alcohol; an ether-based solvent such as diethyl ether, tetrahydrofuran, 1,2-dimethoxyethane, 1,4-dioxane, and cyclopentyl methyl ether; an ester-based solvent such as ethyl acetate, propyl acetate, and methyl propionate; an aromatic hydrocarbon-based solvent such as benzene, toluene, and xylene; an aliphatic hydrocarbon-based solvent such as n-pentane, n-hexane, and n-heptane; an amide-based solvent such as N,N-dimethylformamide, N-methylpyrrolidone, and hexamethylphosphoric acid triamide; a sulfur-containing solvent such as dimethyl sulfoxide and sulfolane; a mixed solvent including two or more solvents among these solvents; and the like.

Among these, an alcohol-based solvent, an ether-based solvent, and a mixed solvent of an alcohol-based solvent and an ether-based solvent are preferable.

The solvent may be used in an appropriate amount taking account of the type of each compound, the reaction scale, and the like. The solvent is normally used in an amount of 1 to 100 g per gram of the hydrazone compound (3).

The reaction proceeds smoothly when the reaction temperature is within the range from −10° C. to the boiling point of the solvent. The reaction time is determined taking account of the reaction scale, and is normally several minutes to several hours.

Production Method 2

The polymerizable compound represented by the formula (I) wherein the group represented by $Z^2$—$Y^8$-$G^2$-$Y^6$-$A^5$-$Y^4$-$A^3$-$Y^2$ is identical to the group represented by $Z^1$—$Y^7$-$G^1$-$Y^5$-$A^4$-$Y^3$-$A^2$-$Y^1$, and $Y^1$ is a group represented by $Y^{11}$—C(=O)—O— (hereinafter referred to as "compound (I')") may be produced as described below.

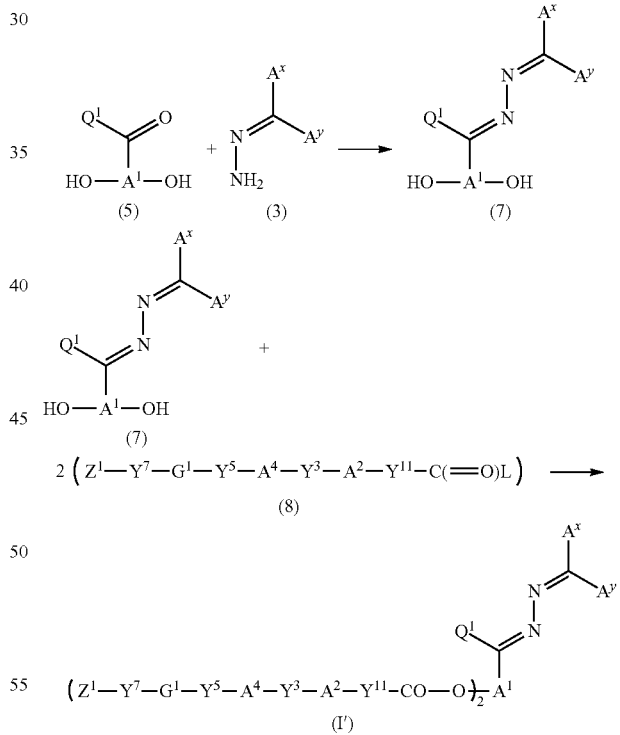

wherein $Y^3$, $Y^5$, $Y^7$, $G^1$, $Z^1$, $A^x$, $A^y$, $A^1$, $A^2$, $A^4$, and $Q^1$ are the same as defined above, $Y^{11}$ is a group whereby $Y^1$ is represented by $Y^{11}$—C(O)—O—, and $Y^1$ is the same as defined above, and L is a leaving group (e.g., hydroxyl group, halogen atom, methanesulfonyloxy group, or p-toluenesulfonyloxy group).

Specifically, the dihydroxy compound that includes a group represented by —C(=O)-$Q^1$ in the molecule (dihydroxy compound (5)) is reacted with the hydrazone compound (3) to obtain the hydroxy compound (7) (step 1), and the hydroxy compound (7) is reacted with the compound represented by the formula (8) (compound (8)) in an amount equal to or more than the 2-fold equivalent (step 2) to produce the compound represented by the formula (I').

In the step 1, the dihydroxy compound (5) is reacted with the hydrazone compound (3) in a solvent in a molar ratio (dihydroxy compound (5):hydrazone compound (3)) of 1:1 to 1:5 (preferably 1:1 to 1:3) to obtain the hydroxy compound (7).

The solvent used in the step 1 is not particularly limited as long as the solvent is inert to the reaction.

Examples of the solvent include those mentioned above in connection with the production method 1. The solvent may be used in an appropriate amount taking account of the type of each compound, the reaction scale, and the like. The solvent is normally used in an amount of 1 to 100 g per gram of the hydrazone compound (3).

In the step 2, the hydroxy compound (7) that has been optionally purified is reacted with the compound (8) in a molar ratio (hydroxy compound (7):compound (8)) of 1:2 to 1:4 (preferably 1:2 to 1:3) to produce the compound (I') with high selectivity in high yield.

When the compound (8) is a compound (carboxylic acid) represented by the formula (8) wherein L is a hydroxyl group, the target product may be obtained by effecting the reaction in the presence of a dehydration-condensation agent (e.g., 1-ethyl-3-(3-dimethylaminopropyl)carbodiimide hydrochloride or dicyclohexylcarbodiimide).

The dehydration-condensation agent is normally used in an amount of 1 to 3 mol based on 1 mol of the compound (8).

When the compound (8) is a compound (acid halide) represented by the formula (8) wherein L is a halogen atom, the target product may be obtained by effecting the reaction in the presence of a base.

Examples of the base include an organic base such as triethylamine and pyridine; and an inorganic base such as sodium hydroxide, sodium carbonate, and sodium hydrogen carbonate.

The base is normally used in an amount of 1 to 3 mol based on 1 mol of the compound (8).

When the compound (8) is a compound (mixed acid anhydride) represented by the formula (8) wherein L is a methanesulfonyloxy group, a p-toluenesulfonyloxy group, or the like, the target product may be obtained in the same manner as in the case where L is a halogen atom. In this case, a compound (mixed acid anhydride) represented by the formula (8) wherein L is a methanesulfonyloxy group, a p-toluenesulfonyloxy group, or the like may be produced by reacting a sulfonyl chloride (e.g., methanesulfonyl chloride or p-toluenesulfonyl chloride) with a compound (carboxylic acid) represented by the formula (8) wherein L is a hydroxyl group, and may be reacted directly with the hydroxy compound (7) without isolating the compound.

Examples of the solvent used in the step 2 include a chlorine-based solvent such as chloroform and methylene chloride; an amide-based solvent such as N-methylpyrrolidone, N,N-dimethylformamide, N,N-dimethylacetamide, and hexamethylphosphoric acid triamide; an ether-based solvent such as 1,4-dioxane, cyclopentyl methyl ether, tetrahydrofuran, tetrahydropyran, and 1,2-dimethoxyethane; a sulfur-containing solvent such as dimethyl sulfoxide and sulfolane; an aromatic hydrocarbon-based solvent such as benzene, toluene, and xylene; an aliphatic hydrocarbon-based solvent such as n-pentane, n-hexane, and n-octane; an alicyclic hydrocarbon-based solvent such as cyclopentane and cyclohexane; a mixed solvent including two or more solvents among these solvents; and the like.

The solvent may be used in an appropriate amount taking account of the type of each compound, the reaction scale, and the like. The solvent is normally used in an amount of 1 to 50 g per gram of the hydroxy compound (7).

The polymerizable compound represented by the formula (I') wherein the groups represented by $Z^1$—$Y^7$-$G^1$-$Y^5$-$A^4$-$Y^3$-$A^2$-$Y^{11}$—C(=O)—O— differ from each other, may be produced by sequentially reacting two different compounds represented by $Z^1$—$Y^7$-$G^1$-$Y^5$-$A^4$-$Y^3$-$A^2$-$Y^{11}$—C(=O)-L stepwise in the same manner as in the case of producing the compound represented by the formula (I').

The hydroxy compound (7) may also be obtained as described below.

(Step 1a)

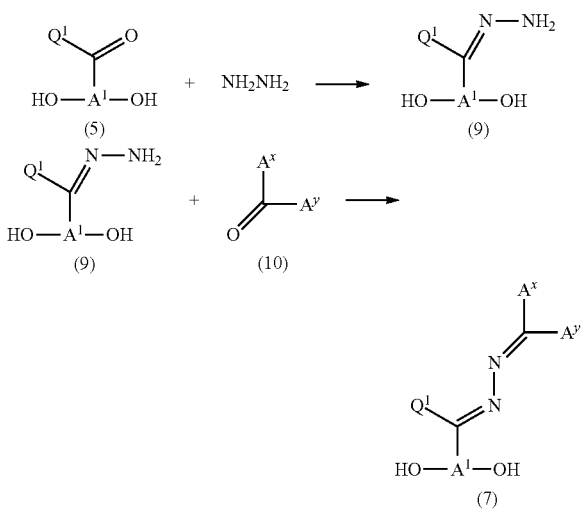

Specifically, hydrazine is reacted with the dihydroxy compound (5) to obtain the hydrazone compound represented by the formula (9), and the hydrazone compound is reacted with the carbonyl compound represented by the formula (10) to obtain the hydroxy compound (7).

Many of the dihydroxy compounds (5) are known compounds, and may be produced using a known method. A commercially available product may be used as the dihydroxy compound (5) either directly or after optional purification.

The hydrazone compound (3) may be produced as described below.

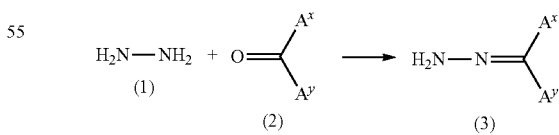

Specifically, the carbonyl compound represented by the formula (2) is reacted with hydrazine (1) in an appropriate solvent in a molar ratio (carbonyl compound (2):hydrazine (1)) of 1:1 to 1:20 (preferably 1:2 to 1:10) to obtain the corresponding hydrazone compound (3). A compound represented by the following formula (2') may be used instead of the carbonyl compound represented by the formula (2).

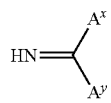 (2')

In this case, the target hydrazone compound (3) can also be obtained.

Hydrazine monohydrate is normally used as hydrazine. A commercially available product may be used directly as hydrazine.

The solvent used for the above reaction is not particularly limited as long as the solvent is inert to the reaction. Examples of the solvent include an alcohol-based solvent such as methyl alcohol, ethyl alcohol, n-propyl alcohol, isopropyl alcohol, n-butyl alcohol, isobutyl alcohol, sec-butyl alcohol, tert-butyl alcohol, n-pentyl alcohol, and amyl alcohol; an ether-based solvent such as diethyl ether, tetrahydrofuran, 1,2-dimethoxyethane, 1,4-dioxane, and cyclopentyl methyl ether; an aromatic hydrocarbon-based solvent such as benzene, toluene, and xylene; an aliphatic hydrocarbon-based solvent such as n-pentane, n-hexane, and n-heptane; an amide-based solvent such as N,N-dimethylformamide, N-methylpyrrolidone, and hexamethylphosphoric acid triamide; a sulfur-containing solvent such as dimethyl sulfoxide and sulfolane; a mixed solvent including two or more solvents among these solvents; and the like.

Among these, an alcohol-based solvent, an ether-based solvent, and a mixed solvent of an alcohol-based solvent and an ether-based solvent are preferable.

The solvent may be used in an appropriate amount taking account of the type of each compound, the reaction scale, and the like. The solvent is normally used in an amount of 1 to 100 g per gram of hydrazine.

The reaction proceeds smoothly when the reaction temperature is within the range from −10° C. to the boiling point of the solvent. The reaction time is determined taking account of the reaction scale, and is normally several minutes to several hours.

The carbonyl compound (4) and the compound (8) may be produced by appropriately bonding and modifying a plurality of known compounds having the desired structure by arbitrarily combining an ether linkage (—O—)-forming reaction, an ester linkage (—C(=O)—O— or —O—C(=O)—)-forming reaction, a carbonate linkage (—O—C(=O)—O—)-forming reaction, and an amide linkage (—C(=O)NH— or —NHC(=O)—)-forming reaction.

An ether linkage may be formed as described below, for example.

(i) A compound represented by D1-hal (wherein hal is a halogen atom; hereinafter the same) and a compound represented by D2-OMet (wherein Met is an alkali metal (mainly sodium); hereinafter the same) are mixed and condensed (Williamson synthesis). Note that D1 and D2 are an arbitrary organic group (hereinafter the same).

(ii) A compound represented by D1-hal and a compound represented by D2-OH are mixed and condensed in the presence of a base (e.g., sodium hydroxide or potassium hydroxide).

(iii) A compound represented by D1-Epo (wherein Epo is an epoxy group) and a compound represented by D2-OH are mixed and condensed in the presence of a base (e.g., sodium hydroxide or potassium hydroxide).

(iv) A compound represented by D1-OFN (wherein OFN is a group that includes an unsaturated bond) and a compound represented by D2-OMet are mixed and subjected to an addition reaction in the presence of a base (e.g., sodium hydroxide or potassium hydroxide).

(v) A compound represented by D1-hal and a compound represented by D2-OMet are mixed and condensed in the presence of copper or cuprous chloride (Ullmann condensation).

An ester linkage and an amide linkage may be formed as described below, for example.

(vi) A compound represented by D1-COOH and a compound represented by D2-OH or D2-NH$_2$ are subjected to dehydration and condensation in the presence of a dehydration-condensation agent (e.g., N,N-dicyclohexylcarbodiimide).

(vii) A compound represented by D1-COOH is reacted with a halogenating agent to obtain a compound represented by D1-CO-hal, and the compound represented by D1-CO-hal is reacted with a compound represented by D2-OH or D2-NH$_2$ in the presence of a base.

(viii) A compound represented by D1-COOH is reacted with an acid anhydride to obtain a mixed acid anhydride, and the mixed acid anhydride is reacted with a compound represented by D2-OH or D2-NH$_2$.

(ix) A compound represented by D1-COOH and a compound represented by D2-OH or D2-NH$_2$ are subjected to dehydration and condensation in the presence of an acid catalyst or a base catalyst.

After completion of the reaction, a post-treatment operation normally employed in synthetic organic chemistry is performed, optionally followed by a known separation/purification means such as column chromatography, recrystallization, or distillation to isolate the target product.

The structure of the target product may be identified by measurement/elemental analysis (e.g., NMR spectrometry, IR spectrometry, or mass spectrometry), and the like.

2) Polymerizable Composition

A polymerizable composition according to one embodiment of the invention includes the polymerizable compound according to one embodiment of the invention, and an initiator. The initiator is used in order to more efficiently polymerize the polymerizable composition according to one embodiment of the invention.

The initiator may be appropriately selected taking account of the type of the polymerizable group included in the polymerizable compound. For example, a radical initiator may be used when the polymerizable group is a radically polymerizable group. An anionic initiator may be used when the polymerizable group is an anionically polymerizable group. A cationic initiator may be used when the polymerizable group is a cationically polymerizable group.

Examples of the radical initiator include a thermal radical generator that is a compound that generates active species that initiate polymerization of the polymerizable compound upon heating; and a photo-radical generator that is a compound that generates active species that initiate polymerization of the polymerizable compound upon exposure to light (exposure light) (e.g., visible rays, ultraviolet rays (e.g., i-line), deep ultraviolet rays, electron beams, or X-rays). It is preferable to use a photo-radical generator.

Examples of the photo-radical generator include an acetophenone-based compound, a biimidazole-based compound, a triazine-based compound, an O-acyloxime-based compound, an onium salt-based compound, a benzoin-based compound, a benzophenone-based compound, an α-diketone-based compound, a polynuclear quinone-based compound, a xanthone-based compound, a diazo-based compound, an imide sulfonate-based compound, and the like. These compounds generate active radicals or an active acid, or both, upon exposure. These photo-radical generators may be used either alone or in combination.

Specific examples of the acetophenone-based compound include
2-hydroxy-2-methyl-1-phenylpropan-1-one,
2-methyl-1-[4-(methylthio)phenyl]-2-morpholinopropan-1-one,
2-benzyl-2-dimethylamino-1-(4-morpholinophenyl)butan-1-one, 1-hydroxycyclohexyl phenyl ketone, 2,2-dimethoxy-1,2-diphenylethan-1-one, 1,2-octanedione,
2-benzyl-2-dimethylamino-4'-morpholinobutyrophenone, and the like.

Specific examples of the biimidazole-based compound include
2,2'-bis(2-chlorophenyl)-4,4',5,5'-tetrakis(4-ethoxycarbonylphenyl)-1,2'-biimidazole,
2,2'-bis(2-bromophenyl)-4,4',5,5'-tetrakis(4-ethoxycarbonylphenyl)-1,2'-biimidazole,
2,2'-bis(2-chlorophenyl)-4,4',5,5'-tetraphenyl-1,2'-biimidazole,
2,2'-bis(2,4-dichlorophenyl)-4,4',5,5'-tetraphenyl-1,2'-biimidazole,
2,2'-bis(2,4,6-trichlorophenyl)-4,4',5,5'-tetraphenyl-1,2'-biimidazole,
2,2'-bis(2-bromophenyl)-4,4',5,5'-tetraphenyl-1,2'-biimidazole,
2,2'-bis(2,4-dibromophenyl)-4,4',5,5'-tetraphenyl-1,2'-biimidazole,
2,2'-bis(2,4,6-tribromophenyl)-4,4',5,5'-tetraphenyl-1,2'-biimidazole, and the like.

When using a biimidazole-based compound as a photoinitiator, it is preferable to use a hydrogen donor in combination with the biimidazole-based compound since sensitivity can be further improved.

The term "hydrogen donor" used herein refers to a compound that can donate a hydrogen atom to radicals generated by the biimidazole-based compound upon exposure. A mercaptan-based compound, an amine-based compound, and the like are preferable as the hydrogen donor.

Examples of the mercaptan-based compound include 2-mercaptobenzothiazole, 2-mercaptobenzoxazole, 2-mercaptobenzimidazole, 2,5-dimercapto-1,3,4-thiadiazole, 2-mercapto-2,5-dimethylaminopyridine, and the like. Examples of the amine-based compound include 4,4'-bis(dimethylamino)benzophenone, 4,4'-bis(diethylamino)benzophenone, 4-diethylaminoacetophenone, 4-dimethylaminopropiophenone, ethyl-4-dimethylaminobenzoate, 4-dimethylaminobenzoic acid, 4-dimethylaminobenzonitrile, and the like.

Specific examples of the triazine-based compound include a triazine-based compound that includes a halomethyl group, such as
2,4,6-tris(trichloromethyl)-s-triazine, 2-methyl-4,6-bis(trichloromethyl)-s-triazine,
2-[2-(5-methylfuran-2-yl)ethenyl]-4,6-bis(trichloromethyl)-s-triazine,
2-[2-(furan-2-yl)ethenyl]-4,6-bis(trichloromethyl)-s-triazine,
2-[2-(4-diethylamino-2-methylphenyl)ethenyl]-4,6-bis(trichloromethyl)-s-triazine,
2-[2-(3,4-dimethoxyphenyl)ethenyl]-4,6-bis(trichloromethyl)-s-triazine,
2-(4-methoxyphenyl)-4,6-bis(trichloromethyl)-s-triazine,
2-(4-ethoxystyryl)-4,6-bis(trichloromethyl)-s-triazine, and
2-(4-n-butoxyphenyl)-4,6-bis(trichloromethyl)-s-triazine.

Specific examples of the O-acyloxime-based compound include
1-[4-(phenylthio)phenyl]-heptane-1,2-dione-2-(O-benzoyloxime),
1-[4-(phenylthio)phenyl]-octane-1,2-dione-2-(O-benzoyloxime),
1-[4-(benzoyl)phenyl]-octane-1,2-dione-2-(O-benzoyloxime),
1-[9-ethyl-6-(2-methylbenzoyl)-9H-carbazol-3-yl]-ethanone-1-(O-acetyloxime),
1-[9-ethyl-6-(3-methylbenzoyl)-9H-carbazol-3-yl]-ethanone-1-(O-acetyloxime),
1-(9-ethyl-6-benzoyl-9h-carbazol-3-yl)-ethanone-1-(O-acetyloxime),
ethanone-1-[9-ethyl-6-(2-methyl-4-tetrahydrofuranylbenzoyl)-9H-carbazol-3-yl]-1-(O-acetyloxime),
ethanone-1-[9-ethyl-6-(2-methyl-4-tetrahydropyranylbenzoyl)-9H-carbazol-3-yl]-1-(O-acetyloxime),
ethanone-1-[9-ethyl-6-(2-methyl-5-tetrahydrofuranylbenzoyl)-9H-carbazol-3-yl]-1-(O-acetyloxime),
ethanone-1-[9-ethyl-6-(2-methyl-5-tetrahydropyranylbenzoyl)-9H-carbazol-3-yl]-1-(O-acetyloxime),
ethanone-1-[9-ethyl-6-{2-methyl-4-(2,2-dimethyl-1,3-dioxolanyl)benzoyl}-9H-carbazol-3-yl]-1-(O-acetyloxime),
ethanone-1-[9-ethyl-6-(2-methyl-4-tetrahydrofuranylmethoxybenzoyl)-9H-carbazol-3-yl]-1-(O-acetyloxime),
ethanone-1-[9-ethyl-6-(2-methyl-4-tetrahydropyranylmethoxybenzoyl)-9H-carbazol-3-yl]-1-(O-acetyloxime),
ethanone-1-[9-ethyl-6-(2-methyl-5-tetrahydrofuranylmethoxybenzoyl)-9H-carbazol-3-yl]-1-(O-acetyloxime),
ethanone-1-[9-ethyl-6-(2-methylbenzoyl)-9H-carbazol-3-yl]-1-(O-acetyloxime),
ethanone-1-[9-ethyl-6-(2-methyl-5-tetrahydropyranylmethoxybenzoyl)-9H-carbazol-3-yl]-1-(O-acetyloxime),
ethanone-1-[9-ethyl-6-{2-methyl-4-(2,2-dimethyl-1,3-dioxolanyl)methoxybenzoyl}-9H-carbazol-3-yl]-1-(O-acetyloxime), and the like.

A commercially available product may be used directly as the photo-radical generator. Specific examples of a commercially available product that may be used as the photo-radical generator include Irgacure 907, Irgacure 184, Irgacure 369, Irgacure 651, Irgacure 819, Irgacure 907, and Irgacure OXE02 (manufactured by BASF); Adekaoptomer N1919 (manufactured by Adeka Corporation); and the like.

Examples of the anionic initiator include an alkyllithium compound; a monolithium salt or a monosodium salt of biphenyl, naphthalene, pyrene, and the like; a polyfunctional initiator such as a dilithium salt and a trilithium salt; and the like.

Examples of the cationic initiator include a proton acid such as sulfuric acid, phosphoric acid, perchloric acid, and trifluoromethanesulfonic acid; a Lewis acid such as boron trifluoride, aluminum chloride, titanium tetrachloride, and tin tetrachloride; an aromatic onium salt or a combination of an aromatic onium salt and a reducing agent; and the like.

These initiators may be used either alone or in combination.

The initiator is normally used to prepare the polymerizable composition according to one embodiment of the invention in an amount of 0.1 to 30 parts by weight, and preferably 0.5 to 10 parts by weight, based on 100 parts by weight of the polymerizable compound.

It is preferable to add a surfactant to the polymerizable composition according to one embodiment of the invention in order to adjust surface tension. The surfactant is not particularly limited, but is preferably a nonionic surfactant. A commercially available product may be used as the nonionic surfactant. Examples of a commercially available product that may be used as the nonionic surfactant include an oligomer having a molecular weight of about several thousand (e.g., "KH-40" manufactured by AGC Seimi Chemical Co., Ltd.), and the like. The surfactant is normally added to the polymerizable composition according to one embodiment of the invention in an amount of 0.01 to 10 parts by weight, and preferably 0.1 to 2 parts by weight, based on 100 parts by weight of the polymerizable compound.

The polymerizable composition according to one embodiment of the invention may further include an additional additive such as an additional copolymerizable monomer, a metal, a metal complex, a dye, a pigment, a fluorescent material, a phosphorescent material, a leveling agent, a thixotropic agent, a gelling agent, a polysaccharide, a UV absorber, an IR (infrared) absorber, an antioxidant, an ion-exchange resin, or a metal oxide (e.g., titanium oxide). Each additive is normally added to the polymerizable composition according to one embodiment of the invention in an amount of 0.1 to 20 parts by weight based on 100 parts by weight of the polymerizable compound.

The polymerizable composition according to one embodiment of the invention may be prepared by mixing and dissolving given amounts of the polymerizable compound according to one embodiment of the invention, the initiator, and an optional additive in an appropriate organic solvent.

Examples of the organic solvent include a ketone such as cyclopentanone, cyclohexanone, and methyl ethyl ketone; an acetate such as butyl acetate and amyl acetate; a halogenated hydrocarbon such as chloroform, dichloromethane, and dichloroethane; an ether such as 1,4-dioxane, cyclopentyl methyl ether, tetrahydrofuran, tetrahydropyran, and 1,3-dioxolane; and the like.

The polymerizable composition thus obtained is useful as a material for producing a polymer according to one embodiment of the invention, or producing an optically anisotropic article according to one embodiment of the invention (described below).

3) Polymer

A polymer according to one embodiment of the invention is (1) a polymer obtained by polymerizing the polymerizable compound according to one embodiment of the invention, or (2) a polymer obtained by polymerizing the polymerizable composition according to one embodiment of the invention.

The term "polymerization" used herein refers to a chemical reaction in a broad sense including a normal polymerization reaction and a crosslinking reaction.

(1) Polymer Obtained by Polymerizing Polymerizable Compound

The polymer obtained by polymerizing the polymerizable compound according to one embodiment of the invention may be a homopolymer of the polymerizable compound according to one embodiment of the invention, a copolymer of two or more types of the polymerizable compound according to one embodiment of the invention, or a copolymer of the polymerizable compound according to one embodiment of the invention and an additional copolymerizable monomer.

Examples of the additional copolymerizable monomer include, but are not limited to, 4'-methoxyphenyl 4-(2-methacryloyloxyethyloxyl)benzoate, biphenyl 4-(6-methacryloyloxyhexyloxyl)benzoate, 4'-cyanobiphenyl 4-(2-acryloyloxyethyloxyl)benzoate, 4'-cyanobiphenyl 4-(2-methacryloyloxyethyloxyl)benzoate, 3',4'-difluorophenyl 4-(2-methacryloyloxyethyloxyl)benzoate, naphthyl 4-(2-methacryloyloxyethyloxyl)benzoate, 4-acryloyloxy-4'-decylbiphenyl, 4-acryloyloxy-4'-cyanobiphenyl, 4-(2-acryloyloxyethyloxy)-4'-cyanobiphenyl, 4-(2-methacryloyloxyethyloxy)-4'-methoxybiphenyl, 4-(2-methacryloyloxyethyloxy)-4'-(4"-fluorobenzyloxy)-biphenyl, 4-acryloyloxy-4'-propylcyclohexylphenyl, 4-methacryloyl-4'-butylbicyclohexyl, 4-acryloyl-4'-amylotolan, 4-acryloyl-4'-(3,4-difluorophenyl)bicyclohexyl, (4-amylphenyl) 4-(2-acryloyloxyethyl)benzoate, (4-(4'-propylcyclohexyl)phenyl) 4-(2-acryloyloxyethyl)benzoate, and the like.

A commercially available product may be used as the additional copolymerizable monomer either directly or after optional purification. Examples of a commercially available product that may be used as the additional copolymerizable monomer include LC-242 (manufactured by BASF) and the like. The compounds disclosed in JP-A-2007-002208, JP-A-2009-173893, JP-A-2009-274984, JP-A-2010-030979, JP-A-2010-031223, JP-A-2011-006360, and the like may also be used as the additional copolymerizable monomer.

A polyfunctional monomer that includes a plurality of polymerizable unsaturated groups (e.g., acryloyl group, methacryloyl group, vinyl group, and allyl group) may also be used as the additional copolymerizable monomer.

Examples of such a polyfunctional monomer include an alkanediol diacrylate such as 1,2-butanediol diacrylate, 1,3-butanediol diacrylate, 1,4-butanediol diacrylate, neopentanediol diacrylate, and 1,6-hexanediol diacrylate; an alkanediol dimethacrylate such as 1,2-butanediol dimethacrylate, 1,3-butanediol dimethacrylate, 1,4-butanediol dimethacrylate, neopentanediol dimethacrylate, and 1,6-hexanediol dimethacrylate; a polyethylene glycol diacrylate such as ethylene glycol diacrylate, diethylene glycol diacrylate, triethylene glycol diacrylate, and tetraethylene glycol diacrylate; a polypropylene glycol diacrylate such as propylene glycol diacrylate, dipropylene glycol diacrylate, tripropylene glycol diacrylate, and tetrapropylene glycol diacrylate; a polyethylene glycol dimethacrylate such as ethylene glycol dimethacrylate, diethylene glycol dimethacrylate, triethylene glycol dimethacrylate, and tetraethylene glycol dimethacrylate; a polypropylene glycol dimethacrylate such as propylene glycol dimethacrylate, dipropylene glycol dimethacrylate, tripropylene glycol dimethacrylate, and tetrapropylene glycol dimethacrylate; a polyethylene glycol divinyl ether such as ethylene glycol divinyl ether, diethylene glycol divinyl ether, triethylene glycol divinyl ether, and tetraethylene glycol divinyl ether; a polyethylene glycol diallyl ether such as ethylene glycol diallyl ether, diethylene glycol diallyl ether, triethylene glycol diallyl ether, and tetraethylene glycol diallyl ether; bisphenol F ethoxylate diacrylate; bisphenol F ethoxylate dimethacrylate; bisphenol A ethoxylate diacrylate; bisphenol A ethoxylate dimethacrylate; trimethylolpropane triacrylate; trimethylolpropane trimethacrylate; trimethylolpropane ethoxylate triacrylate; trimethylolpropane ethoxylate trimethacrylate; trimethylolpropane propoxylate triacrylate; trimethylolpropane propoxylate trimethacrylate; isocyanuric acid ethoxylate triacrylate; glycerol ethoxylate triacrylate; glycerol propoxylate triacrylate; pentaerythritol ethoxylate tetraacrylate; ditrimethylolpropane ethoxylate tetraacrylate; dipentaerythritol ethoxylate hexacrylate; and the like.

The polymerizable compound according to one embodiment of the invention may be (co)polymerized optionally together with the additional copolymerizable monomer in the presence of an appropriate initiator. The initiator may be used in an amount similar to that of the initiator included in the polymerizable composition.

When the polymer according to one embodiment of the invention is a copolymer of the polymerizable compound according to one embodiment of the invention and the additional copolymerizable monomer, the content of structural units derived from the polymerizable compound according to one embodiment of the invention is not particularly limited, but is preferably 50 wt % or more, and more preferably 70 wt % or more, based on the total structural units. When the content of structural units derived from the polymerizable compound is within the above range, a polymer that has a high glass transition temperature (Tg) and high hardness can be obtained.

The polymer (1) may be produced by (A) (co)polymerizing the polymerizable compound optionally together with the additional copolymerizable monomer in an appropriate organic solvent in the presence of an appropriate initiator, isolating the target polymer, dissolving the polymer in an appropriate organic solvent to prepare a solution, applying the solution to an appropriate substrate to obtain a film, and drying the film, followed by optional heating, or (B) applying a solution prepared by dissolving the polymerizable compound in an organic solvent optionally together with the additional copolymerizable monomer to a substrate using a known coating method, removing the solvent, and effecting polymerization by applying heat or activated energy rays, for example.

Examples of the initiator include those mentioned above in connection with the initiator included in the polymerizable composition.

The organic solvent used for polymerization when using the method (A) is not particularly limited as long as the organic solvent is inert. Examples of the organic solvent include an aromatic hydrocarbon such as toluene, xylene, and mesitylene; a ketone such as cyclohexanone, cyclopentanone, and methyl ethyl ketone; an acetate such as butyl acetate and amyl acetate; a halogenated hydrocarbon such as chloroform, dichloromethane, and dichloroethane; an ether such as cyclopentyl methyl ether, tetrahydrofuran, and tetrahydropyran; and the like. Among these, it is preferable to use a compound having a boiling point of 60 to 250° C., and preferably 60 to 150° C., from the viewpoint of handling capability.

Examples of the organic solvent used to dissolve the polymer when implementing the method (A), and the organic solvent used for the method (B), include a ketone-based solvent such as acetone, methyl ethyl ketone, methyl isobutyl ketone, cyclopentanone, and cyclohexanone; an ester-based solvent such as butyl acetate and amyl acetate; a halogenated hydrocarbon-based solvent such as dichloromethane, chloroform, and dichloroethane; an ether-based solvent such as tetrahydrofuran, tetrahydropyran, 1,2-dimethoxyethane, 1,4-dioxane, cyclopentyl methyl ether, 1,3-dioxolane; an aprotic polar solvent such as N,N-dimethylformamide, N,N-dimethylacetamide, dimethyl sulfoxide, γ-butyrolactone, and N-methylpyrrolidone; and the like. Among these, it is preferable to use a compound having a boiling point of 60 to 200° C. from the viewpoint of handling capability. These solvents may be used either alone or in combination.

A substrate formed of a known organic or inorganic material may be used as the substrate. Examples of the organic material include polycycloolefins (e.g., Zeonex and Zeonor (registered trademark; manufactured by Zeon Corporation); Arton (registered trademark; manufactured by JSR Corporation); and Apel (registered trademark; manufactured by Mitsui Chemicals Inc.)), polyethylene terephthalate, polycarbonate, polyimide, polyamide, polymethyl methacrylate, polystyrene, polyvinyl chloride, polytetrafluoroethylene, cellulose, cellulose triacetate, polyethersulfone, and the like. Examples of the inorganic material include silicon, glass, calcite, and the like. It is preferable to use a substrate formed of an organic material.

The substrate may be a single-layer substrate, or may be a laminate.

The substrate is preferably a substrate formed of an organic material, and more preferably a resin film that is formed of the organic material.

The polymer solution (method (A)) or the solution subjected to polymerization (method (B)) may be applied to the substrate using a known coating method. Examples of the coating method include a curtain coating method, an extrusion coating method, a roll coating method, a spin coating method, a dip coating method, a bar coating method, a spray coating method, a slide coating method, a print coating method, and the like.

(2) Polymer Obtained by Polymerizing Polymerizable Composition

The polymer according to one embodiment of the invention can be easily obtained by polymerizing the polymerizable composition according to one embodiment of the invention. It is preferable to use the polymerizable composition that includes the initiator (particularly a photoinitiator) in order to more efficiently effect polymerization.

Specifically, it is preferable to produce the polymer according to one embodiment of the invention using the method (B) that applies the polymerizable composition according to one embodiment of the invention to a substrate, and polymerizes the applied polymerizable composition. Examples of the substrate include a substrate used to produce an optically anisotropic article (described later), and the like.

The polymerizable composition according to one embodiment of the invention may be applied to the substrate using a known coating method (e.g., bar coating method, spin coating method, roll coating method, gravure coating method, spray coating method, die coating method, cap coating method, or dipping method). A known organic solvent may be added to the polymerizable composition according to one embodiment of the invention in order to improve the applicability of the polymerizable composition. In this case, it is preferable to remove the organic solvent by natural drying, drying by heating, drying under reduced pressure, drying by heating under reduced pressure, or the like, after applying the polymerizable composition to the substrate.

The polymerizable compound according to one embodiment of the invention, or the polymerizable composition according to one embodiment of the invention, may be polymerized by applying activated energy rays, or utilizing a thermal polymerization method, for example. It is preferable to polymerize the polymerizable compound or the polymerizable composition by applying activated energy rays since heating is unnecessary (i.e., the reaction can be effected at room temperature). It is preferable to apply light (e.g., ultraviolet rays) to the polymerizable compound or the polymerizable composition since the operation is simple.

The temperature during application is preferably set to 30° C. or less. The dose is normally set to 1 $W/m^2$ to 10 $kW/m^2$, and preferably 5 $W/m^2$ to 2 $kW/m^2$.

A polymer obtained by polymerizing the polymerizable compound according to one embodiment of the invention, or the polymerizable composition according to one embodiment of the invention, may be removed from the substrate, and used alone, or may be used directly as an optical film organic material or the like without removing the polymer from the substrate.

The number average molecular weight of the polymer according to one embodiment of the invention thus obtained is preferably 500 to 500,000, and more preferably 5000 to 300,000. When the number average molecular weight of the polymer is within the above range, the resulting film exhibits high hardness and an excellent handling capability. The number average molecular weight of the polymer may be determined by gel permeation chromatography (GPC) using monodisperse polystyrene as the standard (eluant: tetrahydrofuran).

It is considered that the polymer according to one embodiment of the invention has a structure in which crosslinking points are uniformly present within the molecule, and exhibits a high crosslinking efficiency and excellent hardness.

The polymer according to one embodiment of the invention makes it possible to inexpensively produce an optical film that achieves uniform conversion of polarized light over a wide wavelength band, and exhibits satisfactory performance (e.g., transparency).

4) Optically Anisotropic Article

An optically anisotropic article according to one embodiment of the invention includes (is produced using) the polymer according to one embodiment of the invention.

The optically anisotropic article according to one embodiment of the invention may be obtained by forming an alignment film on a substrate, and forming a liquid crystal layer on the alignment film using the polymer according to one embodiment of the invention.

The alignment film is formed on the surface of the substrate in order to achieve in-plane alignment of an organic semiconductor compound in one direction.

The alignment film may be obtained by applying a solution (alignment film composition) that includes a polymer (e.g., polyimide, polyvinyl alcohol, polyester, polyallylate, polyamideimide, or polyetherimide) to the substrate to form a film, drying the film, and subjecting the film to a rubbing treatment in one direction, for example.

The thickness of the alignment film is preferably 0.001 to 5 μm, and more preferably 0.001 to 1 μm.

The rubbing treatment may be performed on the alignment film or the substrate. The rubbing treatment may be implemented using an arbitrary method. For example, the alignment film may be rubbed in a given direction using a roll around which a cloth or felt formed of synthetic fibers (e.g., nylon) or natural fibers (e.g., cotton) is wound. It is preferable to wash (clean) the alignment film with isopropyl alcohol or the like after completion of the rubbing treatment in order to remove a fine powder (foreign substance) formed during the rubbing treatment, and clean the surface of the alignment film.

The alignment film may be provided with a function of achieving in-plane alignment of a cholesteric liquid crystal layer in one direction by applying polarized ultraviolet rays to the surface of the alignment film.

The liquid crystal layer may be formed on the alignment film using the polymer according to one embodiment of the invention by utilizing the method described above in connection with the polymer according to one embodiment of the invention.

Since the optically anisotropic article according to one embodiment of the invention is produced using the polymer according to one embodiment of the invention, the optically anisotropic article can be produced at low cost, achieves uniform conversion of polarized light over a wide wavelength band, and exhibits satisfactory performance (e.g., transparency).

The optically anisotropic article according to one embodiment of the invention may be applied to a retardation film, an alignment film for a liquid crystal display device (liquid crystal display), a polarizer, a viewing angle-improving film, a color filter, a low-pass filter, an optical polarization prism, an optical filter, and the like.

EXAMPLES

The invention is further described below by way of examples. Note that the invention is not limited to the following examples.

Example 1

Synthesis of Compound 1

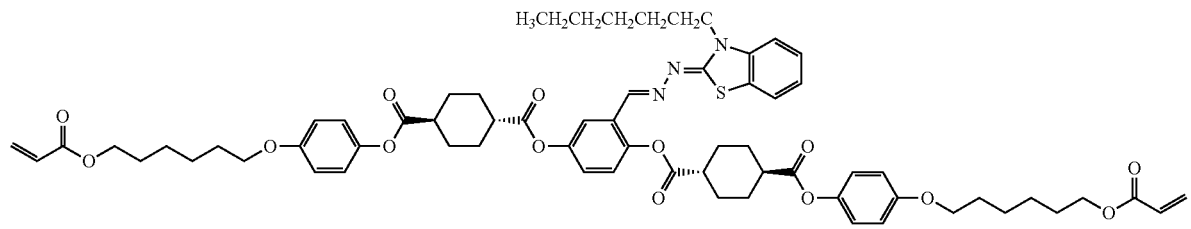

Compound 1

Step 1: Synthesis of Intermediate A

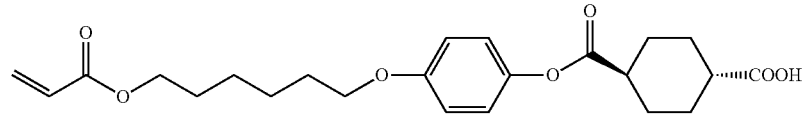

Intermediate A

A three-necked reactor equipped with a thermometer was charged with 17.98 g (104.42 mmol) of trans-1,4-cyclohexanedicarboxylic acid and 180 ml of tetrahydrofuran (THF) under a nitrogen stream. After the addition of 6.58 g (57.43 mmol) of methanesulfonyl chloride to the mixture, the reactor was immersed in a water bath to adjust the temperature of the reaction mixture to 20° C. 6.34 g (62.65 mmol) of triethylamine was added dropwise to the reaction mixture over 10 minutes while maintaining the temperature of the reaction mixture at 20 to 30° C. After the dropwise addition, the mixture was stirred at 25° C. for 2 hours.

After the addition of 0.64 g (5.22 mmol) of 4-(dimethylamino)pyridine and 13.80 g (52.21 mmol) of 4-(6-acryloyloxyhex-1-yloxy)phenol (manufactured by DKSH) to the reaction mixture, the reactor was immersed in a water bath to adjust the temperature of the reaction mixture to 15° C. 6.34 g (62.65 mmol) of triethylamine was added dropwise to the reaction mixture over 10 minutes while maintaining the temperature of the reaction mixture at 20 to 30° C. After the dropwise addition, the mixture was stirred at 25° C. for 2 hours.

After completion of the reaction, 1000 ml of distilled water and 100 ml of a saturated sodium chloride solution were added to the reaction mixture, followed by extraction twice with 400 ml of ethyl acetate. The organic layer was collected, and dried over anhydrous sodium sulfate, and sodium sulfate was filtered off. The solvent was evaporated from the filtrate using a rotary evaporator, and the residue was purified by silica gel column chromatography (THF:toluene=1:9 (volume ratio (hereinafter the same)) to obtain 14.11 g of an intermediate A as a white solid (yield: 65%).

The structure of the target product was identified by $^1$H-NMR.

$^1$H-NMR (500 MHz, DMSO-d$_6$, TMS, δ ppm): 12.12 (s, 1H), 6.99 (d, 2H, J=9.0 Hz), 6.92 (d, 2H, J=9.0 Hz), 6.32 (dd, 1H, J=1.5 Hz, 17.5 Hz), 6.17 (dd, 1H, J=10.0 Hz, 17.5 Hz), 5.93 (dd, 1H, J=1.5 Hz, 10.0 Hz), 4.11 (t, 2H, J=6.5 Hz), 3.94 (t, 2H, J=6.5 Hz), 2.48-2.56 (m, 1H), 2.18-2.26 (m, 1H), 2.04-2.10 (m, 2H), 1.93-2.00 (m, 2H), 1.59-1.75 (m, 4H), 1.35-1.52 (m, 8H)

Step 2: Synthesis of Intermediate B

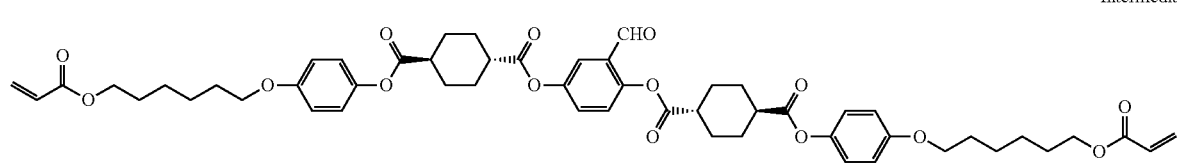

Intermediate B

A three-necked reactor equipped with a thermometer was charged with 4.00 g (9.56 mmol) of the intermediate A synthesized in the step 1 and 60 ml of THF under a nitrogen stream to prepare a homogeneous solution. After the addition of 1.12 g (9.78 mmol) of methanesulfonyl chloride to the solution, the reactor was immersed in a water bath to adjust the temperature of the reaction mixture to 20° C. 1.01 g (9.99 mmol) of triethylamine was added dropwise to the reaction mixture over 5 minutes while maintaining the temperature of the reaction mixture at 20 to 30° C. After the dropwise addition, the mixture was stirred at 25° C. for 2 hours. After the addition of 0.11 g (0.87 mmol) of 4-(dimethylamino)pyridine and 0.60 g (4.35 mmol) of 2,5-dihydroxybenzaldehyde to the reaction mixture, the reactor was immersed in a water bath to adjust the temperature of the reaction mixture to 15° C. 1.10 g (10.87 mmol) of triethylamine was added dropwise to the reaction mixture over 5 minutes while maintaining the temperature of the reaction mixture at 20 to 30° C. After the dropwise addition, the mixture was stirred at 25° C. for 2 hours.

After completion of the reaction, 400 ml of distilled water and 50 ml of a saturated sodium chloride solution were added to the reaction mixture, followed by extraction twice with 750 ml of ethyl acetate. The organic layer was collected, and dried over anhydrous sodium sulfate, and sodium sulfate was filtered off. The solvent was evaporated from the filtrate using a rotary evaporator, and the residue was dissolved in 100 ml of THF. 500 ml of methanol was added to the solution to precipitate crystals, which were filtered off. The crystals were washed with methanol, and dried under vacuum to obtain 2.51 g of an intermediate B as a white solid (yield: 62%).

The structure of the target product was identified by $^1$H-NMR.

$^1$H-NMR (500 MHz, DMSO-d$_6$, TMS, δ ppm): 10.02 (s, 1H), 7.67 (d, 1H, J=3.0 Hz), 7.55 (dd, 1H, J=3.0 Hz, 8.5 Hz), 7.38 (d, 1H, J=8.5 Hz), 6.99-7.04 (m, 4H), 6.91-6.96 (m, 4H), 6.32 (dd, 2H, J=1.5 Hz, 17.5 Hz), 6.17 (dd, 2H, J=10.0 Hz, 17.5 Hz), 5.93 (dd, 2H, J=1.5 Hz, 10.0 Hz), 4.11 (t, 4H, J=6.5 Hz), 3.95 (t, 4H, J=6.5 Hz), 2.56-2.81 (m, 4H), 2.10-2.26 (m, 8H), 1.50-1.76 (m, 16H), 1.33-1.49 (m, 8H)

Step 3: Synthesis of Intermediate C

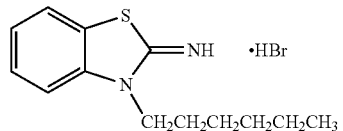

Intermediate C

A three-necked reactor equipped with a thermometer was charged with 1.00 g (6.66 mmol) of 2-aminobenzothiazole and 20 ml of 1-bromohexane under a nitrogen stream. The mixture was heated to 140° C., and reacted for 2 hours. After cooling the mixture to 25° C., 30 ml of toluene was added to the mixture to precipitate crystals, which were filtered off, washed with toluene, and dried under vacuum to obtain 1.52 g of an intermediate C as a white solid (yield: 72%).

The structure of the target product was identified by $^1$H-NMR.

$^1$H-NMR (500 MHz, DMSO-d$_6$, TMS, δ ppm): 12.17 (s, 2H), 8.02 (dd, 1H, J=1.0 Hz, 8.0 Hz), 7.74 (d, 1H, J=8.0 Hz), 7.58 (dt, 1H, J=1.0 Hz, 8.0 Hz), 7.43 (dt, 1H, J=1.0 Hz, 8.0 Hz), 4.26 (t, 2H, J=7.5 Hz), 1.62-1.72 (m, 2H), 1.22-1.43 (m, 6H), 0.86 (t, 3H, J=7.0 Hz)

Step 4: Synthesis of intermediate D

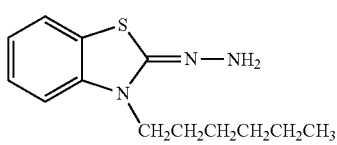

Intermediate D

A three-necked reactor equipped with a thermometer was charged with 1.00 g (3.17 mmol) of the intermediate C, 0.79 g (15.86 mmol) of hydrazine monohydrate, and 15 ml of ethylene glycol under a nitrogen stream to prepare a homogeneous solution. The solution was heated to 140° C., and reacted for 2.5 hours. After cooling the reaction mixture to 25° C., 200 ml of distilled water was added to the reaction mixture, followed by extraction twice with 50 ml of ethyl acetate. The organic layer was dried over anhydrous sodium sulfate, and sodium sulfate was removed by filtration. The filtrate was concentrated using a rotary evaporator, and the concentrate was purified by silica gel column chromatography (toluene:THF=9:1) to obtain 0.51 g of an intermediate D as a light yellow solid (yield: 64%).

The structure of the target product was identified by $^1$H-NMR.

$^1$H-NMR (500 MHz, DMSO-d$_6$, TMS, δ ppm): 7.45 (dd, 1H, J=1.0 Hz, 7.5 Hz), 7.20 (dt, 1H, J=1.0 Hz, 7.5 Hz), 7.03 (d, 1H, J=7.5 Hz), 6.91 (dt, 1H, J=1.0 Hz, 7.5 Hz), 5.00 (s, 2H), 3.84 (t, 2H, J=7.5 Hz), 1.55-1.65 (m, 2H), 1.21-1.36 (m, 6H), 0.85 (t, 3H, J=7.0 Hz)

Step 5: Synthesis of Compound 1

A three-necked reactor equipped with a thermometer was charged with 1.0 g (1.06 mmol) of the intermediate B and 40 ml of THF under a nitrogen stream to prepare a solution. After the addition of 0.22 ml (0.22 mmol) of a 1 N hydrochloric acid aqueous solution and 0.32 g (1.28 mmol) of the intermediate D to the solution, the mixture was reacted at 25° C. for 1 hour. The reaction mixture was concentrated using a rotary evaporator. 200 ml of methanol was added to the concentrate to precipitate crystals, which were filtered off. The crystals were purified by silica gel column chromatography (chloroform:THF=100:2.5) to obtain 1.12 g of a compound 1 as a light yellow solid (yield: 90%).

The structure of the target product was identified by $^1$H-NMR.

$^1$H-NMR (500 MHz, CDCl$_3$, TMS, δ ppm): 8.35 (s, 1H), 7.82 (m, 1H), 7.43 (dd, 1H, J=1.0 Hz, 7.5 Hz), 7.26-7.30 (m, 1H), 7.01-7.12 (m, 4H), 6.98 (d, 2H, J=9.0 Hz), 6.98 (d, 2H, J=9.0 Hz), 6.88 (d, 4H, J=9.0 Hz), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 4.17 (t, 4H, J=6.5 Hz), 4.09 (t, 2H, J=7.5 Hz), 3.94 (t, 4H, J=6.5 Hz), 2.53-2.76 (m, 4H), 2.24-2.40 (m, 8H), 1.63-1.87 (m, 18H), 1.28-1.56 (m, 14H), 0.90 (t, 3H, J=7.0 Hz)

Synthesis Example 1

Synthesis of Compound 1r

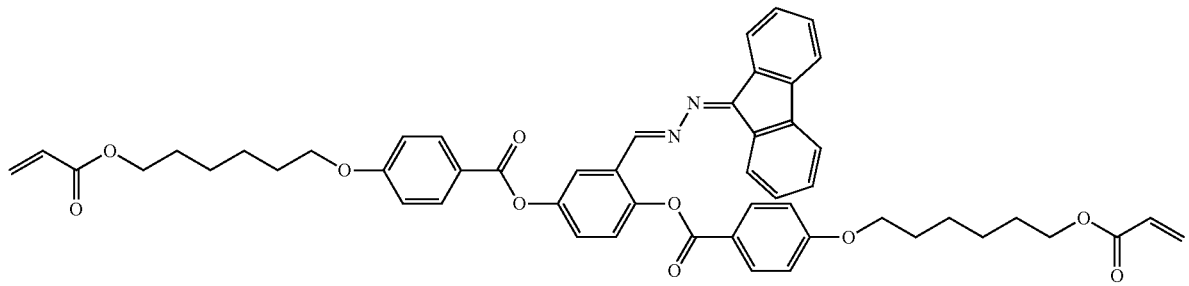

Compound 1r

Step 1: Synthesis of Intermediate α

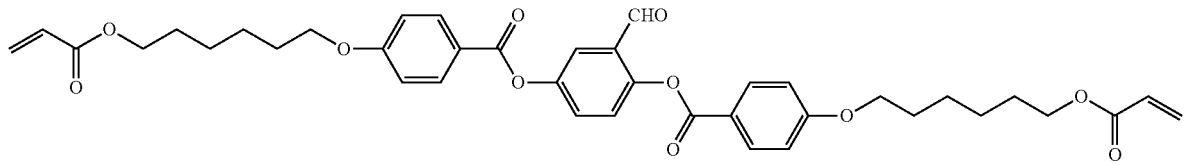

Intermediate α

A four-necked reactor equipped with a thermometer was charged with 20 g (144.8 mmol) of 2,5-dihydroxybenzaldehyde, 105.8 g (362.0 mmol) of 4-(6-acryloylhex-1-yloxy) benzoic acid (manufactured by DKSH Japan K.K.), 5.3 g (43.4 mmol) of 4-(dimethylamino)pyridine, and 200 ml of N-methylpyrrolidone under a nitrogen stream to prepare a solution. After the addition of 83.3 g (434.4 mmol) of 1-ethyl-3-(3-dimethylaminopropyl)carbodiimide hydrochloride to the solution, the mixture was stirred at 25° C. for 12 hours.

After completion of the reaction, the reaction mixture was added to 1.5 l of water, followed by extraction with 500 ml of ethyl acetate. The ethyl acetate layer was dried over anhydrous sodium sulfate, and sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=9:1) to obtain 75 g of an intermediate α as a white solid (yield: 75.4%).

The structure of the target product was identified by $^1$H-NMR.

$^1$H-NMR (400 MHz, CDCl$_3$, TMS, δ ppm): 10.20 (s, 1H), 8.18-8.12 (m, 4H), 7.78 (d, 1H, J=2.8 Hz), 7.52 (dd, 1H, J=2.8 Hz, 8.7 Hz), 7.38 (d, 1H, J=8.7 Hz), 7.00-6.96 (m, 4H), 6.40 (dd, 2H, J=1.4 Hz, 17.4 Hz), 6.12 (dd, 2H, J=10.6 Hz, 17.4 Hz), 5.82 (dd, 2H, J=1.4 Hz, 10.6 Hz), 4.18 (t, 4H, J=6.4 Hz), 4.08-4.04 (m, 4H), 1.88-1.81 (m, 4H), 1.76-1.69 (m, 4H), 1.58-1.42 (m, 8H)

Step 2: Synthesis of Intermediate β

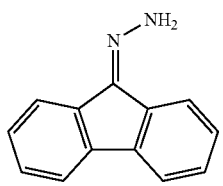

Intermediate β

A four-necked reactor equipped with a thermometer was charged with 5 g (27.7 mmol) of 9-fluorenone, 13.9 g (277.7 mmol) of hydrazine monohydrate, and 50 ml of 1-propanol under a nitrogen stream to prepare a solution, which was stirred at 25° C. for 16 hours. After completion of the reaction, a solid that precipitated was filtered off, and washed with 1-propanol to obtain 2.2 g of an intermediate β as a yellow solid. The resulting solid was air-dried, and used directly for the subsequent reaction without performing purification.

Step 3: Synthesis of Compound 1

A four-necked reactor equipped with a thermometer was charged with 3.0 g (4.37 mmol) of the intermediate α, 1.1 g (5.68 mmol) of the intermediate β, 80 ml of ethanol, and 40 ml of THF under a nitrogen stream to prepare a solution. A solution prepared by dissolving 0.1 g (0.44 mmol) of (±)-10-camphorsulfonic acid in 3 ml of THF was slowly added to the solution. The mixture was then stirred at 25° C. for 2 hours.

After completion of the reaction, the reaction mixture was added to 300 ml of saturated sodium bicarbonate water, and extracted twice with 100 ml of chloroform. The chloroform layer was collected, washed with 200 ml of a saturated sodium chloride solution, and dried over anhydrous sodium sulfate, and sodium sulfate was filtered off.

Chloroform was evaporated from the filtrate under reduced pressure using a rotary evaporator to obtain a yellow solid. The yellow solid was purified by silica gel column chromatography (toluene:ethyl acetate=8:2) to obtain 1.8 g of a compound 1r as a yellow solid (yield: 47.7%).

The structure of the target product was identified by $^1$H-NMR.

$^1$H-NMR (400 MHz, CDCl$_3$, TMS, δ ppm): 8.65 (s, 1H), 8.29 (d, 1H, J=7.3 Hz), 8.21-8.16 (m, 5H), 7.82 (d, 1H, J=7.3 Hz), 7.60-7.57 (m, 2H), 7.43-7.25 (m, 6H), 7.01-6.96 (m, 4H), 6.402 (dd, 1H, J=1.8 Hz, 17.4 Hz), 6.398 (dd, 1H, J=1.8 Hz, 17.4 Hz), 6.122 (dd, 1H, J=10.5 Hz, 17.4 Hz), 6.117 (dd, 1H, J=10.5 Hz, 17.4 Hz), 5.820 (dd, 1H, J=1.8 Hz, 10.5 Hz), 5.816 (dd, 1H, J=1.8 Hz, 10.5 Hz), 4.18 (t, 2H, J=6.6 Hz), 4.17 (t, 2H, J=6.6 Hz), 4.06 (t, 2H, J=6.4 Hz), 4.05 (t, 2H, J=6.4 Hz), 1.87-1.80 (m, 4H), 1.76-1.68 (m, 4H), 1.59-1.42 (m, 8H)

Synthesis Example 2

Synthesis of Compound 2r

Compound 2r

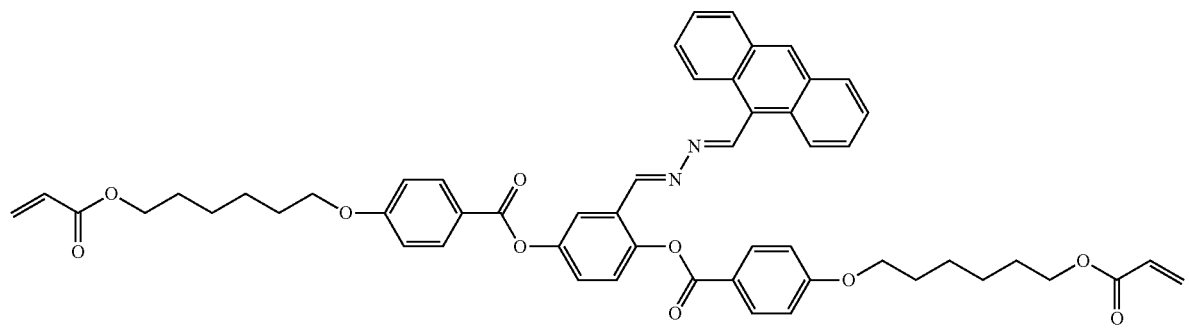

Step 1: Synthesis of

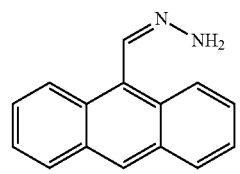

Intermediate γ

A four-necked reactor equipped with a thermometer was charged with 3.6 g (71.9 mmol) of hydrazine monohydrate and 30 ml of ethanol under a nitrogen stream to prepare a solution. A solution prepared by dissolving 3 g (14.5 mmol) of 9-anthracene carboxaldehyde in 30 ml of THF was slowly added dropwise to the solution. The mixture was then stirred at 25° C. for 1.5 hours.

After completion of the reaction, the reaction mixture was added to 200 ml of saturated sodium bicarbonate water, and extracted twice with 100 ml of chloroform. The chloroform layer was collected, washed with 200 ml of a saturated sodium chloride solution, and dried over anhydrous sodium sulfate, and sodium sulfate was filtered off Chloroform was evaporated from the filtrate under reduced pressure using a rotary evaporator to obtain 2.5 g of an intermediate γ as a yellow solid. The resulting solid was dried, and used directly for the subsequent reaction without performing purification.
Step 2: Synthesis of Compound 2r A four-necked reactor equipped with a thermometer was charged with 3.0 g (4.37 mmol) of the intermediate α, 1.2 g (5.24 mmol) of the intermediate γ, and 30 ml of THF under a nitrogen stream to prepare a solution. A solution prepared by dissolving 0.1 g (0.44 mmol) of (±)-10-camphorsulfonic acid in 3 ml of THF was slowly added to the solution. The mixture was then stirred at 25° C. for 2 hours.

After completion of the reaction, the reaction mixture was added to 300 ml of saturated sodium bicarbonate water, and extracted twice with 100 ml of ethyl acetate. The ethyl acetate layer was collected, washed with 200 ml of a saturated sodium chloride solution, and dried over anhydrous sodium sulfate, and sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=95:5) to obtain 2.1 g of a compound 2r as a yellow solid (yield: 54.1%).

The structure of the target product was identified by $^1$H-NMR.

$^1$H-NMR (400 MHz, CDCl$_3$, TMS, δ ppm): 9.74 (s, 1H), 8.95 (s, 1H), 8.57-8.53 (m, 3H), 8.20-8.18 (m, 4H), 8.14 (d, 1H, J=2.7 Hz), 8.02-8.00 (m, 2H), 7.56-7.47 (m, 4H), 7.42 (dd, 1H, J=2.7 Hz, 8.7 Hz), 7.36 (d, 1H, J=8.7 Hz), 7.00-6.96 (m, 4H), 6.404 (dd, 1H, J=1.4 Hz, 17.4 Hz), 6.384 (dd, 1H, J=1.4 Hz, 17.4 Hz), 6.126 (dd, 1H, J=8.7 Hz, 17.4 Hz), 6.100 (dd, 1H, J=8.7 Hz, 17.4 Hz), 5.824 (dd, 1H, J=1.4 Hz, 8.7 Hz), 5.798 (dd, 1H, J=1.4 Hz, 8.7 Hz), 4.18 (t, 2H, J=6.4 Hz), 4.16 (t, 2H, J=6.4 Hz), 4.07 (t, 2H, J=6.4 Hz), 4.02 (t, 2H, J=6.4 Hz), 1.89-1.78 (m, 4H), 1.77-1.66 (m, 4H), 1.58-1.44 (m, 8H)

Measurement of Phase Transition Temperature 10 mg of each compound (compounds 1, 1r, and 2r) was weighed, and placed in a solid state between two glass substrates provided with a polyimide alignment film subjected to a rubbing treatment (manufactured by E.H.C. Co. Ltd.). The substrates were placed on a hot plate, heated from 40° C. to 250° C., and cooled to 40° C. A change in structure during a change in temperature was observed using a polarizing microscope ("ECLIPSE LV100 POL" manufactured by Nikon Corporation).

The phase transition temperature measurement results are shown in Table 1. In Table 1, "C" refers to "crystal", "N" refers to "nematic", and "I" refers to "isotropic". The term "crystal" means that the test compound was in a solid phase, the term "nematic" means that the test compound was in a nematic liquid crystal phase, and the term "isotropic" means that the test compound was in an isotropic liquid phase.

TABLE 1

|  | Compound | Phase transition temperature |
|---|---|---|
| Example 2 | Compound 1 | C ⇌ N ⇌ I (121° C. / 72° C.) (220° C. / 215° C.) |
| Comparative Example 1 | Compound 1r | C ⇌ N ⇌ I (129° C. / 40° C. or less) (109° C.) |
| Comparative Example 2 | Compound 2r | C ⇌ N ⇌ I (138° C. / 40° C. or less) (84° C.) |

Example 2

1.0 g of the compound 1 obtained in Example 1, 30 mg of Adekaoptomer N-1919 (manufactured by Adeka Corporation) (photo initiator), and 100 mg of a 1% cyclopentanone solution of KH-40 (manufactured by AGC Seimi Chemical Co., Ltd.) (surfactant) were dissolved in 2.3 g of cyclopentanone. The solution was filtered through a disposable filter having a pore size of 0.45 μm to prepare a polymerizable composition 1.

Comparative Example 1

1.0 g of the compound 1r obtained in Synthesis Example 1, 30 mg of Adekaoptomer N-1919 (manufactured by Adeka Corporation) (photoinitiator), and 100 mg of a 1% cyclopentanone solution of KH-40 (manufactured by AGC Seimi Chemical Co., Ltd.) (surfactant) were dissolved in 4.0 g of cyclopentanone. The solution was filtered through a disposable filter having a pore size of 0.45 μm to prepare a polymerizable composition 1r.

Comparative Example 2

1.0 g of the compound 2r obtained in Synthesis Example 2, 30 mg of Adekaoptomer N-1919 (manufactured by Adeka Corporation) (photoinitiator), and 100 mg of a 1% cyclopentanone solution of KH-40 (manufactured by AGC Seimi Chemical Co., Ltd.) (surfactant) were dissolved in 4.0 g of cyclopentanone. The solution was filtered through a disposable filter having a pore size of 0.45 μm to prepare a polymerizable composition 2r.

Measurement of Retardation and Evaluation of Wavelength Dispersion (i-1) Formation of Liquid Crystal Layer Using Polymerizable Composition The polymerizable composition 1 was applied to a transparent glass substrate (provided with a polyimide alignment film subjected to a rubbing treatment) (manufactured by E.H.C. Co., Ltd.) using a #4 wire bar. The resulting film was dried for 1 minute at the temperature shown in Table 2, and subjected to an alignment treatment for 1 minute at the temperature shown in Table 2 to form a liquid crystal layer. Ultraviolet rays were applied to the liquid crystal layer at a dose of 2000 mJ/cm$^2$ at the temperature shown in Table 2 to effect polymerization to prepare a wavelength dispersion measurement sample.

Measurement of Retardation and Evaluation of Wavelength Dispersion (i-2) Formation of Liquid Crystal Layer Using Polymerizable Composition The polymerizable composition 1r or 2r was applied to a transparent glass substrate (provided with a polyimide alignment film subjected to a rubbing treatment) (manufactured by E.H.C. Co., Ltd.) using a #6 wire bar. The resulting film was dried for 1 minute at the temperature shown in Table 2, and subjected to an alignment treatment for 1 minute at the temperature shown in Table 2 to form a liquid crystal layer. Ultraviolet rays were applied to the liquid crystal layer at a dose of 2000 mJ/cm$^2$ at the temperature shown in Table 2 to effect polymerization to prepare a wavelength dispersion measurement sample.

(ii) Measurement of Retardation

The retardation between 400 nm and 800 nm was measured using the sample utilizing an ellipsometer ("M2000U" manufactured by J. A. Woollam).

(iii) Evaluation of Wavelength Dispersion

The wavelength dispersion was evaluated based on the values α and β that were calculated by the following expressions using the measured retardation.

α=(retardation at 449.9 nm)/(retardation at 548.5 nm)

β=(retardation at 650.2 nm)/(retardation at 548.5 nm)

The value α is smaller than 1, and the value β is larger than 1 when an ideal wideband wavelength dispersion (reverse wavelength dispersion) is achieved. The values α and β are almost identical when a flat wavelength dispersion is achieved. The value α is larger than 1, and the value β is smaller than 1 when a normal dispersion is achieved.

A flat wavelength dispersion that ensures that the values α and β are almost identical is preferable, and a reverse wavelength dispersion that ensures that the value α is smaller than 1, and the value β is larger than 1, is particularly preferable.

Table 2 shows the thickness (μm) of the liquid crystal polymer films obtained by polymerizing the polymerizable compositions, the retardation (Re) at a wavelength of 548.5 nm, and the values α and β.

TABLE 2

|  | Polymerizable composition | Polymerizable compound | Drying temperature (° C.) | Alignment treatment temperature (° C.) | Exposure temperature (° C.) | Film thickness (μm) | Re (548.5 nm) | α | β |
|---|---|---|---|---|---|---|---|---|---|
| Example 2 | 1 | Compound 1 | 130 | 23 | 80 | 1.570 | 94.67 | 0.616 | 1.089 |
| Comparative Example 1 | 1r | Compound 1r | 135 | 80 | 23 | 1.325 | 111.20 | 0.805 | 1.032 |
| Comparative Example 2 | 2r | Compound 2r | 145 | 65 | 23 | 1.351 | 125.57 | 0.851 | 0.849 |

Evaluation of Transparency

The light transmittance (at 300 to 800 nm) of each wavelength dispersion measurement sample prepared as described above was measured using a UV spectrophotometer ("V-570" manufactured by JASCO Corporation).

Table 3 shows the light transmittance at 400, 426, and 450 nm that may significantly vary depending on coloration of a film. A film that is colored to only a small extent (e.g., exhibits high transparency) has high light transmittance at 400 nm, 426 nm, and 450 nm.

TABLE 3

|  | Polymerizable composition | Polymerizable compound | Light transmittance (% T) | | |
|---|---|---|---|---|---|
|  |  |  | 400 nm | 426 nm | 450 nm |
| Example 2 | 1 | Compound 1 | 15.49 | 78.80 | 87.64 |
| Comparative Example 1 | 1r | Compound 1r | 0.12 | 7.60 | 78.76 |
| Comparative Example 2 | 2r | Compound 2r | 0.16 | 8.55 | 80.55 |

As shown in Tables 2 and 3, the polymerizable composition 1 of Example 2 had a reverse wavelength dispersion (preferable wavelength dispersion), and had high light transmittance at 400 nm, 426 nm, and 450 nm (i.e., exhibited high transparency due to little coloration).

The polymerizable composition 1r of Comparative Example 1 had a reverse wavelength dispersion, but had low light transmittance at 400 nm and 426 nm (i.e., exhibited inferior transparency). The polymerizable composition 2r of Comparative Example 2 did not have a reverse wavelength dispersion, and had low light transmittance at 400 nm and 426 nm (i.e., exhibited inferior transparency).

The invention claimed is:

1. A polymerizable compound represented by a formula (I),

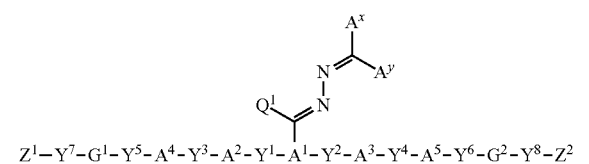

$Z^1-Y^7-G^1-Y^5-A^4-Y^3-A^2-Y^1-A^1-Y^2-A^3-Y^4-A^5-Y^6-G^2-Y^8-Z^2$ wherein $Y^1$ to $Y^8$ are independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—, R$^1$ is a hydrogen atom or an alkyl group having 1 to 6 carbon atoms, $G^1$ and $G^2$ are independently a substituted or unsubstituted divalent linear aliphatic group having 1 to 20 carbon atoms that optionally includes —O—, —S—, —O—C(=O)—, —C(=O)—O—, —O—C(=O)—O—, —NR$^2$—C(=O)—, —C(=O)—NR$^2$—, —NR$^2$—, or —C(=O)—, provided that a case where the aliphatic group includes two or more contiguous —O— or —S— is excluded, R$^2$ is a hydrogen atom or an alkyl group having 1 to 6 carbon atoms, $Z^1$ and $Z^2$ are independently an alkenyl group having 2 to 10 carbon atoms that is substituted with a halogen atom, or unsubstituted, $A^x$ is an organic group having 2 to 30 carbon atoms that includes at least one aromatic ring selected from a group consisting of an aromatic hydrocarbon ring and a heteroaromatic ring, $A^y$ is a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, —C(=O)—R$^3$, —SO$_2$—R$^4$, or an organic group having 2 to 30 carbon atoms that includes at least one aromatic ring selected from a group consisting of an aromatic hydrocarbon ring and a heteroaromatic ring, provided that the aromatic ring included in $A^x$ and the aromatic ring optionally included in $A^y$ are either substituted or unsubstituted, and $A^x$ and $A^y$ are optionally bonded to each other to form a ring, $R^3$ is a substituted or unsubstituted alkyl group having 1 to 12 carbon atoms, a substituted or unsubstituted alkenyl group having 2 to 12 carbon atoms, or a substituted or unsubstituted cycloalkyl group having 3 to 12 carbon atoms, $R^4$ is an alkyl group having 1 to 12 carbon atoms, an alkenyl group having 2 to 12 carbon atoms, a phenyl group, or a 4-methylphenyl group, $A^1$ is a substituted or unsubstituted trivalent aromatic group, $A^2$ and $A^3$ are independently a substituted or unsubstituted divalent alicyclic hydrocarbon group having 3 to 30 carbon atoms, $A^4$ and $A^5$ are independently a substituted or unsubstituted divalent aromatic group having 6 to 30 carbon atoms, and $Q^1$ is a hydrogen atom, or a substituted or unsubstituted alkyl group having 1 to 6 carbon atoms.

2. The polymerizable compound according to claim 1, wherein a total number of π electrons included in $A^x$ and $A^y$ is 4 to 24.

3. The polymerizable compound according to claim 1, wherein $A^1$ is a substituted or unsubstituted trivalent benzene ring group, or a substituted or unsubstituted trivalent naphthalene ring group.

4. The polymerizable compound according to claim 1, wherein $Y^1$ to $Y^8$ are independently a chemical single bond, —O—, —O—C(=O)—, —C(=O)—O—, or —O—C(=O)—O—.

5. The polymerizable compound according to claim 1, wherein $Z^1$ and $Z^2$ are independently $CH_2$=CH—, $CH_2$=C($CH_3$)—, or $CH_2$=C(Cl)—.

6. The polymerizable compound according to claim 1, wherein $G^1$ and $G^2$ are independently a substituted or unsubstituted divalent aliphatic group having 1 to 12 carbon atoms that optionally includes —O—, —O—C(=O)—, —C(=O)—O—, or —C(=O)—, provided that a case where the aliphatic group includes two or more contiguous —O— is excluded.

7. The polymerizable compound according to claim 1, wherein $G^1$ and $G^2$ are independently a divalent alkylene group having 1 to 12 carbon atoms.

8. A polymerizable composition comprising at least one polymerizable compound according to claim 1.

9. A polymerizable composition comprising the polymerizable compound according to claim 1, and an initiator.

10. A polymer comprising the polymerizable compound according to claim 1.

11. The polymer according to claim 10, the polymer being a liquid crystalline polymer.

12. An optically anisotropic article comprising the polymer according to claim 11.

13. A polymerizable composition comprising at least one polymerizable compound according to claim 2.

14. A polymerizable composition comprising at least one polymerizable compound according to claim 3.

15. A polymerizable composition comprising at least one polymerizable compound according to claim 4.

16. A polymerizable composition comprising at least one polymerizable compound according to claim 5.

17. A polymerizable composition comprising at least one polymerizable compound according to claim 6.

18. A polymerizable composition comprising at least one polymerizable compound according to claim 7.

19. A polymerizable composition comprising the polymerizable compound according to claim 2, and an initiator.

20. A polymerizable composition comprising the polymerizable compound according to claim 3, and an initiator.

\* \* \* \* \*